(12) United States Patent
Sowden et al.

(10) Patent No.: US 8,545,887 B2
(45) Date of Patent: Oct. 1, 2013

(54) MODIFIED RELEASE DOSAGE FORMS

(75) Inventors: Harry S. Sowden, Glenside, PA (US); David Wynn, Huntingdon Valley, PA (US); Shun-Por Li, Lansdale, PA (US); Der-Yang Lee, Flemington, NJ (US); Martin Thomas, Lake Worth, FL (US)

(73) Assignee: McNeil-PPC, Inc., Skillman, NJ (US)

( * ) Notice: Subject to any disclaimer, the term of this patent is extended or adjusted under 35 U.S.C. 154(b) by 1446 days.

(21) Appl. No.: 10/476,530

(22) PCT Filed: Sep. 28, 2002

(86) PCT No.: PCT/US02/31117
§ 371 (c)(1),
(2), (4) Date: May 27, 2004

(87) PCT Pub. No.: WO03/026629
PCT Pub. Date: Apr. 3, 2003

(65) Prior Publication Data
US 2004/0213849 A1    Oct. 28, 2004

(51) Int. Cl.
| A61J 3/06 | (2006.01) |
|---|---|
| A61K 9/20 | (2006.01) |
| B30B 11/00 | (2006.01) |
| A61K 9/24 | (2006.01) |
| G06F 17/30 | (2006.01) |

(52) U.S. Cl.
USPC .......................... 424/472; 424/464; 424/474

(58) Field of Classification Search
USPC ........................................................ 424/472
See application file for complete search history.

(56) References Cited

U.S. PATENT DOCUMENTS

| 582,438 A | 5/1897 | Scheidler |
|---|---|---|
| 599,865 A | 3/1898 | Richards |
| 2,307,371 A | 1/1943 | Hileman |
| 2,996,431 A | 8/1961 | Barry |
| 3,085,942 A | 4/1963 | Magid et al. |
| 3,146,169 A | 8/1964 | Stephenson et al. |
| 3,185,626 A | 5/1965 | Baker |
| 3,279,995 A | 10/1966 | Reid |
| 3,627,583 A | 12/1971 | Troy et al. |
| 3,670,065 A | 6/1972 | Eriksson et al. |
| 3,726,622 A | 4/1973 | DeTroyer et al. |
| 3,760,804 A | 9/1973 | Higuchi et al. |
| 3,804,570 A | 4/1974 | Hoschele et al. |
| 3,832,252 A | 8/1974 | Higuchi et al. |
| 4,076,819 A | 2/1978 | Maffrand |
| 4,097,606 A | 6/1978 | Chavkin et al. |
| 4,111,202 A | 9/1978 | Theeuwes |
| 4,139,589 A | 2/1979 | Beringer et al. |
| 4,173,626 A | 11/1979 | Dempski et al. |
| 4,198,390 A | 4/1980 | Rider |
| 4,218,433 A | 8/1980 | Kooichi et al. |
| 4,230,693 A | 10/1980 | Izzo et al. |
| 4,271,206 A | 6/1981 | Fariel et al. |
| 4,273,793 A | 6/1981 | Fareil et al. |
| 4,279,926 A | 7/1981 | Bruzzese et al. |
| 4,292,017 A | 9/1981 | Doepel |
| 4,322,449 A | 3/1982 | Voss et al. |
| 4,362,757 A | 12/1982 | Chen et al. |
| 4,371,516 A | 2/1983 | Gregory et al. |
| 4,372,942 A | 2/1983 | Cimiluca |
| 4,392,493 A | 7/1983 | Niemeijer |
| 4,425,332 A | 1/1984 | James |

(Continued)

FOREIGN PATENT DOCUMENTS

| CN | 1099262 A | 1/1995 |
|---|---|---|
| CN | 1130867 A | 11/1996 |

(Continued)

OTHER PUBLICATIONS

Lai, Jin-Wang, "Drug Release from Inert Matrices of Modified Geometry", The University of Iowa, University Microfilms International, 1985, pp. 29-59.

(Continued)

*Primary Examiner* — Michael G Hartley
*Assistant Examiner* — Nabila G Ebrahim
(74) *Attorney, Agent, or Firm* — Laura A. Donnelly

(57) ABSTRACT

A dosage form comprises: (a) at least one active ingredient: (b) a core having a first surface portion upon which resides a first coating and a second surface portion which is substantially free of the first coating; and (c) a shell which resides upon at least a portion of the second surface portion, wherein the shell comprises a different material from the first coating. In another embodiment, the dosage form comprises: (a) at least one active ingredient; (b) a core comprising a center portion having an exterior surface and an annular portion having an exterior surface and an interior surface, wherein the annular portion interior surface is in contact with at least a portion of the center portion exterior surface, and a coating resides on at least a portion of the annular portion exterior surface; and (c) a shell which resides upon at least a portion of the exterior surface of the center portion, wherein the shell comprises a different material than the impermeable coating. In another embodiment, the dosage form comprises: (a) at least one active ingredient; (b) a core having an outer surface and a cavity which extends at least partially through the core such that the core outer surface has at least a first opening therein; (c) a first coating which resides on at least a portion of the core outer surface, wherein the first shell portion comprises a different material from the first coating; and (d) a first shell portion which is adjacent to the first opening and covers at least the first opening.

40 Claims, 7 Drawing Sheets

(56) References Cited

U.S. PATENT DOCUMENTS

| | | | |
|---|---|---|---|
| 4,449,983 | A | 5/1984 | Cortese et al. |
| 4,473,526 | A | 9/1984 | Buhler et al. |
| RE31,764 | E | 12/1984 | Voss et al. |
| 4,517,205 | A | 5/1985 | Aldrich |
| 4,518,335 | A | 5/1985 | Pujari |
| 4,533,345 | A | 8/1985 | Louw |
| 4,543,370 | A | 9/1985 | Porter et al. |
| 4,544,345 | A | 10/1985 | Buhler et al. |
| 4,564,525 | A | 1/1986 | Mitchell et al. |
| 4,569,650 | A | 2/1986 | Kramer |
| 4,576,604 | A | 3/1986 | Guittard et al. |
| 4,610,884 | A | 9/1986 | Lewis et al. |
| 4,643,894 | A | 2/1987 | Porter et al. |
| 4,661,521 | A | 4/1987 | Salpekar et al. |
| 4,663,147 | A | 5/1987 | DePrince |
| 4,683,256 | A | 7/1987 | Porter et al. |
| 4,686,212 | A | 8/1987 | Ducatman et al. |
| 4,725,441 | A | 2/1988 | Porter et al. |
| 4,749,575 | A | 6/1988 | Rotman |
| 4,757,090 | A | 7/1988 | Salpekar et al. |
| 4,762,719 | A | 8/1988 | Forester |
| 4,781,714 | A | 11/1988 | Eckenhoff et al. |
| 4,786,505 | A | 11/1988 | Lovgren et al. |
| 4,801,461 | A | 1/1989 | Hamel et al. |
| 4,802,924 | A | 2/1989 | Woznicki et al. |
| 4,803,076 | A | 2/1989 | Ranade |
| 4,813,818 | A | 3/1989 | Sanzone |
| 4,816,262 | A | 3/1989 | McMullen |
| 4,820,524 | A | 4/1989 | Berta |
| 4,828,841 | A | 5/1989 | Porter et al. |
| 4,851,226 | A | 7/1989 | Julian et al. |
| 4,853,230 | A | 8/1989 | Lovgren et al. |
| 4,857,330 | A | 8/1989 | Stephens et al. |
| 4,863,742 | A | 9/1989 | Panoz et al. |
| 4,865,849 | A | 9/1989 | Conte et al. |
| 4,873,231 | A | 10/1989 | Smith |
| 4,882,167 | A | 11/1989 | Jang |
| 4,894,236 | A | 1/1990 | Jang |
| 4,906,478 | A | 3/1990 | Valentine et al. |
| 4,929,446 | A | 5/1990 | Bartolucci |
| 4,965,027 | A | 10/1990 | Takahashi |
| 4,978,483 | A | 12/1990 | Redding, Jr. |
| 4,980,169 | A | 12/1990 | Oppenheimer et al. |
| 4,980,170 | A | 12/1990 | Schneider et al. |
| 4,983,394 | A | 1/1991 | Hussein et al. |
| 4,984,240 | A | 1/1991 | Keren-Zvi et al. |
| 4,999,226 | A | 3/1991 | Schock et al. |
| 5,002,970 | A | 3/1991 | Eby, III |
| 5,004,614 | A | 4/1991 | Staniforth |
| 5,032,406 | A | 7/1991 | Dansereau et al. |
| 5,059,112 | A | 10/1991 | Wieser |
| 5,075,114 | A | 12/1991 | Roche |
| 5,089,270 | A | 2/1992 | Hampton |
| 5,133,892 | A | 7/1992 | Chun et al. |
| 5,145,868 | A | 9/1992 | von Sprecher et al. |
| 5,146,730 | A | 9/1992 | Sadek et al. |
| 5,169,645 | A | 12/1992 | Shukla et al. |
| 5,188,840 | A | 2/1993 | Iida et al. |
| 5,200,191 | A | 4/1993 | Steele et al. |
| 5,200,193 | A | 4/1993 | Radebaugh et al. |
| 5,213,738 | A | 5/1993 | Hampton et al. |
| 5,213,808 | A | 5/1993 | Ba-Shalom et al. |
| 5,228,916 | A | 7/1993 | Berta |
| 5,229,164 | A | 7/1993 | Pins et al. |
| 5,232,706 | A | 8/1993 | Coll |
| 5,275,822 | A | 1/1994 | Valentine et al. |
| 5,286,497 | A | 2/1994 | Hendrickson et al. |
| 5,368,863 | A | 11/1994 | Eckenhoff et al. |
| 5,391,378 | A | 2/1995 | Sanderson |
| 5,393,533 | A | 2/1995 | Versic |
| 5,405,617 | A | 4/1995 | Gowan, Jr. et al. |
| 5,405,642 | A | 4/1995 | Gilis et al. |
| 5,407,686 | A * | 4/1995 | Patel et al. .................... 424/468 |
| 5,415,868 | A | 5/1995 | Smith et al. |
| 5,424,075 | A | 6/1995 | Daher et al. |
| 5,427,614 | A | 6/1995 | Wittwer et al. |
| 5,433,951 | A | 7/1995 | Serajuddin et al. |
| 5,436,026 | A | 7/1995 | Berta |
| 5,456,920 | A | 10/1995 | Matoba et al. |
| 5,459,983 | A | 10/1995 | Sadek et al. |
| 5,462,747 | A | 10/1995 | Radebaugh et al. |
| 5,464,631 | A | 11/1995 | Hoover et al. |
| 5,464,633 | A | 11/1995 | Conte et al. |
| 5,489,436 | A | 2/1996 | Hoy et al. |
| 5,510,385 | A | 4/1996 | Stroppolo et al. |
| 5,511,361 | A | 4/1996 | Sauter |
| 5,538,125 | A | 7/1996 | Berta |
| 5,558,879 | A | 9/1996 | Chen |
| 5,559,110 | A | 9/1996 | Aungst |
| 5,578,336 | A | 11/1996 | Monte |
| 5,593,696 | A | 1/1997 | McNally et al. |
| 5,609,010 | A | 3/1997 | Sauter |
| 5,610,214 | A * | 3/1997 | Olson ............................ 524/311 |
| 5,614,207 | A | 3/1997 | Shah et al. |
| 5,626,875 | A | 5/1997 | Rodes et al. |
| 5,627,971 | A | 5/1997 | Miernik |
| 5,630,871 | A | 5/1997 | Jordan |
| 5,641,536 | A | 6/1997 | Lech et al. |
| 5,654,005 | A | 8/1997 | Chen et al. |
| 5,658,589 | A | 8/1997 | Parekh et al. |
| 5,679,406 | A | 10/1997 | Berta |
| 5,681,584 | A | 10/1997 | Savastano et al. |
| 5,683,719 | A * | 11/1997 | Newton ........................ 424/474 |
| 5,711,961 | A | 1/1998 | Reiner et al. |
| 5,738,874 | A | 4/1998 | Conte et al. |
| 5,753,265 | A | 5/1998 | Bergstrand et al. |
| 5,795,588 | A | 8/1998 | Sauter |
| 5,807,579 | A | 9/1998 | Vilkov et al. |
| 5,807,580 | A | 9/1998 | Luber |
| 5,817,338 | A | 10/1998 | Bergstrand et al. |
| 5,824,338 | A | 10/1998 | Jacobs et al. |
| 5,827,535 | A | 10/1998 | Stone |
| 5,827,874 | A | 10/1998 | Meyer et al. |
| 5,830,501 | A | 11/1998 | Dong et al. |
| 5,830,502 | A | 11/1998 | Dong et al. |
| 5,834,035 | A | 11/1998 | Osada et al. |
| 5,837,301 | A | 11/1998 | Arnott et al. |
| 5,849,327 | A | 12/1998 | Berliner et al. |
| 5,853,760 | A | 12/1998 | Cremer |
| 5,861,173 | A | 1/1999 | Nishioka et al. |
| 5,871,781 | A | 2/1999 | Myers et al. |
| 5,912,013 | A | 6/1999 | Rudnic et al. |
| 5,942,034 | A | 8/1999 | Brehant et al. |
| 5,980,944 | A | 11/1999 | Stevens et al. |
| 5,997,903 | A | 12/1999 | Dietrich et al. |
| 5,997,905 | A | 12/1999 | McTeigue et al. |
| 6,001,391 | A | 12/1999 | Zeidler et al. |
| 6,013,281 | A | 1/2000 | Lundberg et al. |
| 6,022,554 | A * | 2/2000 | Lee et al. ....................... 424/423 |
| 6,077,541 | A | 6/2000 | Chen et al. |
| 6,090,401 | A | 7/2000 | Gowan et al. |
| 6,096,340 | A | 8/2000 | Chen et al. |
| 6,103,257 | A | 8/2000 | Nisonoff |
| 6,103,260 | A | 8/2000 | Luber et al. |
| 6,110,499 | A * | 8/2000 | Shivanand et al. ............ 424/473 |
| 6,110,500 | A | 8/2000 | Kim |
| 6,117,479 | A | 9/2000 | Hogan et al. |
| 6,120,802 | A | 9/2000 | Breitenbach et al. |
| 6,123,861 | A | 9/2000 | Santini et al. |
| 6,149,939 | A | 11/2000 | Strumor et al. |
| 6,149,943 | A | 11/2000 | McTeigue et al. |
| 6,159,499 | A | 12/2000 | Seth |
| 6,174,548 | B1 | 1/2001 | Chen et al. |
| 6,183,776 | B1 | 2/2001 | Depui et al. |
| 6,200,590 | B1 | 3/2001 | Eley |
| 6,207,198 | B1 | 3/2001 | Seth |
| 6,217,902 | B1 | 4/2001 | Tanner et al. |
| 6,224,910 | B1 | 5/2001 | Ullah et al. |
| 6,248,355 | B1 | 6/2001 | Seth |
| 6,248,361 | B1 | 6/2001 | Johnson et al. |
| 6,248,760 | B1 | 6/2001 | Wilhelmsen |
| 6,264,985 | B1 | 7/2001 | Cremer |
| 6,270,805 | B1 | 8/2001 | Chen et al. |
| 6,274,162 | B1 | 8/2001 | Steffinino et al. |

| | | | |
|---|---|---|---|
| 6,294,200 B1 | 9/2001 | Conte et al. | |
| 6,322,819 B1 | 11/2001 | Burnside et al. | |
| 6,331,316 B1 | 12/2001 | Ullah et al. | |
| 6,350,398 B1 | 2/2002 | Breitenbach et al. | |
| 6,365,185 B1* | 4/2002 | Ritschel et al. | 424/473 |
| 6,372,252 B1 | 4/2002 | Blume et al. | |
| 6,375,963 B1 | 4/2002 | Repka et al. | |
| 6,394,094 B1 | 5/2002 | McKenna et al. | |
| 6,428,810 B1 | 8/2002 | Bergstrand et al. | |
| 6,489,346 B1 | 12/2002 | Phillips | |
| 6,555,139 B2 | 4/2003 | Sharma | |
| 6,569,457 B2 | 5/2003 | Ullah et al. | |
| 6,602,522 B1 | 8/2003 | Chen et al. | |
| 6,613,354 B2 | 9/2003 | Depui et al. | |
| 6,726,927 B2 | 4/2004 | Chen | |
| 6,730,646 B1 | 5/2004 | Waschenbach et al. | |
| 6,742,646 B2 | 6/2004 | Sowden et al. | |
| 6,767,200 B2 | 7/2004 | Sowden et al. | |
| 6,837,696 B2 | 1/2005 | Sowden et al. | |
| 6,982,094 B2 | 1/2006 | Sowden | |
| 7,122,143 B2 | 10/2006 | Sowden et al. | |
| 2001/0001280 A1 | 5/2001 | Dong et al. | |
| 2002/0028240 A1 | 3/2002 | Sawada et al. | |
| 2002/0051807 A1 | 5/2002 | Faour et al. | |
| 2002/0082299 A1 | 6/2002 | Meyer | |
| 2003/0059466 A1* | 3/2003 | Seth | 424/474 |
| 2003/0060393 A1 | 3/2003 | Waschenbach et al. | |
| 2003/0068367 A1 | 4/2003 | Sowden et al. | |
| 2003/0070903 A1 | 4/2003 | Sowden et al. | |
| 2003/0072799 A1 | 4/2003 | Sowden et al. | |
| 2003/0086973 A1 | 5/2003 | Sowden et al. | |
| 2003/0124183 A1 | 7/2003 | Sowden et al. | |
| 2003/0190362 A1 | 10/2003 | Sackler et al. | |
| 2003/0232082 A1 | 12/2003 | Li et al. | |
| 2003/0235616 A1 | 12/2003 | Sowden et al. | |
| 2005/0074514 A1 | 4/2005 | Anderson | |
| 2006/0269603 A1 | 11/2006 | Brown Miller et al. | |

FOREIGN PATENT DOCUMENTS

| | | |
|---|---|---|
| CN | 1183047 A | 5/1998 |
| DE | 27 10 307 | 9/1977 |
| DE | 36 29 994 A1 | 3/1988 |
| DE | 198 34 180 A1 | 2/2000 |
| DE | 19925710 A | 12/2000 |
| DE | 199 54 420 A1 | 5/2001 |
| DE | 199 63 569 A1 | 7/2001 |
| EP | 1 372 040 | 12/1971 |
| EP | 0 088 556 B1 | 9/1983 |
| EP | 60023 B1 | 8/1984 |
| EP | 237200 B1 | 2/1987 |
| EP | 0 239 983 B1 | 10/1987 |
| EP | 0 325 492 A1 | 7/1989 |
| EP | 0 387 885 B1 | 9/1990 |
| EP | 0 455 599 A1 | 11/1991 |
| EP | 0 294 993 B1 | 12/1991 |
| EP | 0 861 659 A1 | 2/1992 |
| EP | 0 481 547 A1 | 4/1992 |
| EP | 0 531 524 B1 | 3/1993 |
| EP | 247983 B1 | 7/1993 |
| EP | 0 572 731 A1 | 12/1993 |
| EP | 0 646 650 A2 | 4/1995 |
| EP | 0 788 790 A2 | 2/1996 |
| EP | 496437 B1 | 7/1996 |
| EP | 740938 | 11/1996 |
| EP | 0 864 324 B1 | 3/1997 |
| EP | 519144 B1 | 8/1997 |
| EP | 619854 B1 | 3/1998 |
| EP | 834516 B1 | 4/1998 |
| EP | 861659 A | 9/1998 |
| EP | 0 950 402 B1 | 2/1999 |
| EP | 1 029 892 B1 | 8/2000 |
| EP | 1 077 065 A1 | 2/2001 |
| EP | 1138661 A1 | 10/2001 |
| FR | 2011960 | 3/1970 |
| FR | 2 604 904 A1 | 4/1988 |
| GB | 759081 | 10/1956 |
| GB | 866681 | 4/1961 |
| GB | 994 742 | 5/1961 |
| GB | 888 038 | 1/1962 |
| GB | 936 386 | 9/1963 |
| GB | 1 144 915 | 3/1969 |
| GB | 1372040 A | 10/1974 |
| GB | 1 464 388 | 2/1977 |
| GB | 1510772 | 5/1978 |
| GB | 2 197 778 A | 6/1988 |
| GB | 2 284 760 A | 6/1995 |
| JP | SHO 61 125691 | 5/1986 |
| JP | 63-10719 | 1/1988 |
| JP | HEI 3 232815 | 10/1991 |
| JP | HEI 5 345721 | 12/1993 |
| JP | 7-242535 | 9/1995 |
| NL | 86 602 556 | 5/1988 |
| WO | 89/11968 | 12/1989 |
| WO | 92/22284 A | 12/1992 |
| WO | WO 94/06416 A1 | 3/1994 |
| WO | WO 94/07470 A1 | 4/1994 |
| WO | 95/02396 | 1/1995 |
| WO | WO 95/02396 A1 | 1/1995 |
| WO | WO 95/15156 A1 | 6/1995 |
| WO | WO 97/06695 A1 | 2/1997 |
| WO | WO 97/15293 A2 | 5/1997 |
| WO | 97/49384 | 12/1997 |
| WO | WO 98/20870 A1 | 5/1998 |
| WO | WO 99/02136 A1 | 1/1999 |
| WO | 99/06157 | 2/1999 |
| WO | WO 99/32092 A1 | 7/1999 |
| WO | WO 99/51209 A1 | 10/1999 |
| WO | WO 99/56730 A1 | 11/1999 |
| WO | 99/62496 A1 | 12/1999 |
| WO | WO 00/18447 A2 | 4/2000 |
| WO | WO 00/25755 A1 | 5/2000 |
| WO | 01/28558 | 4/2001 |
| WO | 01/49815 A2 | 7/2001 |
| WO | 01/58433 | 8/2001 |
| WO | 01/85437 A1 | 11/2001 |
| WO | WO 02/11702 A2 | 2/2002 |
| WO | WO 02/19833 A2 | 3/2002 |
| WO | 03/007917 A1 | 1/2003 |
| WO | 03/026626 A | 4/2003 |
| WO | 03/028620 A | 4/2003 |
| WO | 03/063840 A2 | 8/2003 |
| WO | 03/080026 A | 10/2003 |
| WO | 2004/010978 A | 2/2004 |
| WO | 2004/066982 A | 8/2004 |
| WO | 2004/112756 A | 12/2004 |
| WO | 2006/047493 A | 5/2006 |

OTHER PUBLICATIONS

Sangalli, M.E., et al., "Inert Monolithic Device with Central Hole for Constant Drug Release", Proceed. Intern: Symp. Control. Rel. Biosct. Meter., 20 (1993), Controlled Release Society, Inc., pp. 316-317.

Hansson, Arne G., et al., "Perforated Coated Tablets for Controlled Release of Drugs at a Constant Rate", Journal of Pharmaceutical Sciences, Apr. 1988, vol. 77, No. 4, pp. 322-324.

Hsieh, Dean S.T., et al., "Zero-Order Controlled-Release Polymer Matrices for Micro- and Macromolecules". Journal of Pharmaceutical Sciences, Jan. 1983, vol. 72, No. 1, pp. 17-22.

Cleave, J.P., "Some geometrical considerations concerning the design of tablets", J. Pharm. Pharmacol. 1965, pp. 698-702.

Nelson, K.G., et al., "Constant-Release Diffusion Systems—Rate Control by Means of Geometric Configuration", American Chemical Society, 1987, Chap. 24, pp. 325-340.

Desai, S.J., et al., "Investigation of Factors Influencing Release of Solid Drug Dispersed in Inert Matrices", Journal of Pharmaceutical Sciences, Oct. 1965, vol. 54, No. 10, pp. 1459-1464.

Higuchi, T., "Mechanism of Sustained-Action Medication—Theoretical Analysis of Rate of Release of Solid Drugs Dispersed in Solid Matrices", Journal of Pharmaceutical Sciences, Dec. 1963, vol. 52, No. 12, pp. 1145-1149.

Higuchi, Takeru, "Rate of Release of Medicaments from Ointment Bases Containing Drugs in Suspension", Journal of Pharmaceutical Sciences, Oct. 1961, vol. 50, No. 10, pp. 874-875.

Cobby, John, et al., "Influence of Shape Factors on Kinetics of Drug Release from Matrix Tablets I: Theoretical", Journal of Pharmaceutical Sciences, May 1974, vol. 63, No. 5, pp. 725-732.

Cobby, John, et al., "Influence of Shape Factors on Kinetics of Drug Release from Matrix Tablets II: Experimental", Journal of Pharmaceutical Sciences, May 1974, vol. 63, No. 5, pp. 732-737.

Lipper, R.A., et al., "Analysis of Theoretical Behavior of a Proposed Zero-Order Drug Delivery System", Journal of Pharmaceutical Sciences, Feb. 1977, vol. 66, No. 2, pp. 163-164.

Samuelov, Y., et al., "Sustained Release of Drugs from Ethylcellulose-Polyethylene Glycol Films and Kinetics of Drug Release", Journal of Pharmaceutical Sciences, Mar. 1979, vol. 68, No. 3, pp. 325-329.

Kim, Cherng-ju, "Compressed Donut-Shaped Tablets with Zero-Order Release Kinetics", Pharmaceutical Research, Jul. 1994, vol. 12, No. 7, pp. 1045-1048.

"Electrostatics in Continuous Tablet Coating", Manufacturing Chemist, Oct. 1998, vol. 69, No. 10, pp. 13-16.

Elizabeth Carbide Die Co., Inc., "The Elizabeth Companies Tablet Design Training Manual," p. 7, McKeesport, PA.

Catellani, P.L. et al., "Centrifugal die fillign system in a new rotary tablet machine", International Journal of Pharmaceutics, 88 (1992), pp. 285-291.

Cuff, George et al., "A Preliminary Evaluation of Injection Moldign as a Technology to Produce Tablets", Pharmaceutical Technology (1998), Jun. 1998, pp. 96-106.

Lachman, Leon et al., "Chapter II—Tablets", The Theory and Practice of Industrial Pharmacy, (1986), pp. 293-345.

International Search Report dated Feb. 20, 2003 for PCT/US02/31115.

International Search Report dated Feb. 20, 2003 for PCT/US02/31164.

International Search Report dated Jan. 8, 2004 for PCT/US03/08891.

International Search Report dated Feb. 11, 2003 for PCT/US02/31024.

International Search Report dated Feb. 26, 2003 for PCT/US02/31022.

International Search Report dated Feb. 6, 2003 for PCT/US02/31163.

International Search Report dated Feb. 10, 2009 for PCT/US09/009201.

European Search Report EP05253780 dated Aug. 2006.

Ceschel, G.C., et al., "Sugar Coating of Tablets", Bollettino Chimico Farmaceutico, 1980, pp. 127-134, vol. 119, Milan Italy.

Edwards, W.P.P., "Pan Coating". The Science of Sugar Confectionery, 2000, pp. 95-100, 1st Edition, The Royal Society of Chemistry, London, England.

Eith, L., et al., "Injection-Moulded Drug-Delivery Systems", Manufacturing Chemist (Jan. 1987), pp. 21-25.

Fegely, Kurt A., et al. The Effect of Tablet Shape on the Perception of High Gloss Film Coating System, Opaglos 2, High Gloss Film Coating System, COLORCON, Mar. 18, 2002.

Gunsel, Willian., C. et al. "Compression-Coated and Layer Tablets", Pharmaceutical Dosage Forms-Tablets, 1989, pp. 247-284. 2nd Edtion, vol. 1, Marcel Dekker, Inc. New York.

Itoh. International Journal of Pharmaceutics 238 (2002) 153-160.

Leiberman et al. Pharmaceutical Dosage Forms-Tablets, vol. 2, 2nd ed., Marcel Dekker Inc., 1990, pp. 213-217, 327-329.

Maffione, G., et al., "High-Viscosity HPMC as a Film-Coating Agent", Drug Development and Industrial Pharmacy, 1993, pp. 2043-2053, vol. 19, No. 16, Marcel Dekker, Inc. New York.

Minifie, Bernard C., Chocolate, Cocoa and Confectionary: Science and Technology, Jan. 1980, pp. 608-613, 2nd Edition, AVI Publishing Company, Inc., Westport, CT.

Porter, Stuart C., PhD., "Tablet Coating—Part 1", Drug Cosmet, Ind., May 1981, pp. 46-53 and 86-93, vol. 128.

Remington The Science and Practice of Pharmacy, pp. 208-209 (2000).

Rosato, Dominick V. et al., Injection Molding Handbook, 1986, Van Nostrand Reinhold Company.

USP 24, 2000 Version, 19-20 and 856 (1999).

Vehicle.Http://www2.merriam-webster.com/cgi-bin/mwmednim. Accessed Apr. 18, 2009.

Schneider, H. et al. "Contribution to Sugar Coating Tablets" Pharmaceutica Acta Helvetiae, pp. 394-410, vol. 43. Nov. 30, 1967.

* cited by examiner

MODIFIED RELEASE DOSAGE FORMS

BACKGROUND OF THE INVENTION

1. Field of the Invention

This invention relates to modified release dosage forms such as modified release pharmaceutical compositions. More particularly, this invention relates to modified release dosage forms having partial coatings, for example dosage forms partially coated by first material for controlling the surface area through which dissolution of at least one active ingredient contained within the dosage form takes place upon contacting of the dosage form with a liquid medium.

2. Background Information

Modified release pharmaceutical dosage forms have long been used to optimize drug delivery and enhance patient compliance, especially by reducing the number of doses of medicine the patient must take in a day. For this purpose, it is often desirable to modify the rate of release of drug (one preferred type of active ingredient) from a dosage form into the gastrointestinal (g.i.) fluids of a patient, especially to slow the release to provide prolonged action of the drug in the body. In many cases, it is particularly desirable to provide a constant (i.e. zero-order) release rate of the drug. For patients taking a particular medication on a chronic basis, matching the rate of drug absorption into the circulatory system with its rate of metabolism and excretion from the body could enable achievement of a steady state in which a relatively constant level of drug is maintained in the blood. This can have the advantageous effect of minimizing undesirable side effects which may occur at high blood levels, while maintaining a therapeutic level of the active ingredient (e.g. drug) in the body.

The rate at which an orally delivered pharmaceutical active ingredient reaches its site of action in the body depends on a number of factors, including the rate and extent of drug absorption through the g.i. mucosa. To be absorbed into the circulatory system (blood), the drug must first be dissolved in the g.i. fluids. For many drugs, diffusion across the g.i. membranes is relatively rapid compared to dissolution. In these cases, the dissolution of the active ingredient is the rate limiting step in drug absorption, and controlling the rate of dissolution allows the formulator to control the rate of drug absorption into the circulatory system of a patient.

The dissolution rate of a drug in the g.i. fluids depends, among other things, on the drug's solubility and the effective surface area of contact between dissolving drug particles and the dissolution medium. The Nernst-Brunner equation describes the dissolution rate of a drug:

$$dC/dt = (D K_2 S)(1/\nu h)(C_s - C_t)$$

where $dC/dt$ is the drug dissolution rate, $D$ is the diffusion coefficient for the drug, $K$ is a dissolution constant, $h$ is the effective thickness of the diffusion layer, $S$ is the surface area of contact between the drug and the dissolution medium, $C_s$ is the solubility of the drug in the medium (i.e. the concentration of a saturated solution at the surface of the dissolving particle), and $C_t$ is the concentration of drug in the bulk solution at a time t. In the body, the absorption process constantly removes drug from the g.i. tract, usually at a rate faster than that of drug dissolution. This creates what is known as a "sink" condition, where $C_s$, the concentration of drug in the bulk solution, is much less than $C_s$, the concentration of drug in the saturated region at the surface of the dissolving particle.

The primary non-constant terms in this model are $S$, the surface area of contact between the drug and the dissolution medium, and $h$, the effective thickness of the diffusion layer.

In a typical sustained release matrix tablet, the surface area of contact between the drug and dissolution medium decreases over time, while in a diffusional matrix system, the pathlength for diffusion increases over time, as the dissolution "front" recedes from the surface towards the center of the dosage form. The combination of these effects results in a decrease in dissolution rate of the drug over time.

Various dosage forms have been proposed to approach a constant dissolution rate by employing dosage form shapes in which the surface area of contact between the drug and dissolution medium increase at the same rate as the path-length for diffusion. Most involve coating a portion of the dosage form with an impermeable layer to control the surface area available for dissolution of the drug. See for example, U.S. Pat. Nos. 3,146,169; 3,851,638; 4,663,147; 4,816,262; and 6,110,500. One shape of particular interest has been that of a torus. Another has been that of a truncated cone. The primary limitation of such designs has been laborious manufacturing processes which typically include making a core, coating the core with impermeable material, then removing a portion of the core and coating to create the area for drug dissolution. These types of processes have not been shown to be suitable for commercial scale manufacture.

U.S. Pat. No. 4,803,076 discloses a tablet press for use in the manufacture of a tablet in the approximate shape of a truncated cone, as well as an apparatus for removal of a portion of the coated dosage form in order to expose an area for dissolution of the drug. However, the dosage form disclosed therein suffers from the limitation of possessing a flat cylinder or disc shaped central portion, defined by the straight die walls, and a "land" area defined by the perimeter of the upper and lower punches in the compression machine.

There remains an unmet need for a commercially efficient method of producing a partial coating on a dosage form. Such partial coatings would be useful for controlling the surface area through which drug is released from the dosage form, including providing a surface area for drug release from the dosage form that remains constant during the drug release period; and providing a surface area for drug release from the dosage form that increases during the drug release period. The apparatus and methods described in copending U.S. patent application Ser. No. 09/966,497, pages 27-51 and Ser. No. 09/966,450, pages 57-63, the disclosures of which are incorporated herein by reference, advantageously enable manufacture of partially coated dosage forms without the need for a partial coating removal step.

It would additionally be desirable to have a method for making such partially coated dosage forms with a further shell portion, residing upon at least a portion of the uncoated core surface, for example to deliver an immediate release loading dose of one or more active ingredients; or to confer a unique elegant appearance. It would be particularly desirable for the shell portion to reside upon and cover only the uncoated portion of the core surface, and not the first coating material. In would further be desirable to make the shell portion optionally removable by the consumer or healthcare professional prior to ingestion of the dosage form in order to customize dosing. Another beneficial use for such partially coated dosage forms include as containers for holding liquid or solid materials, which may be removed from the dosage form for example by removing the shell portion, and pouring through the uncoated portion prior to use. It would additionally be desirable to have a modified release dosage form comprising an inactive core having a specialized shape or structure, and comprising for example swelling or gelling excipients, which effect the release of active ingredient from one or more shell compartments.

It would also be desirable to coat non-conventionally shaped dosage forms that provide constant controlled release rates by virtue of their shape with a shell of a more regular shape to facilitate swallowing, or reduce friability (susceptibility to breakage). For example it would be useful to have dosage forms comprising a core in the shape of a torus or truncated cone containing an active ingredient therein, protected by a spheroid or elypsoid shaped shell. Such dosage forms would be easy to swallow, maintain their structural integrity during handling and shipping, and yet provide the functional benefits conferred by the shape of the core. The apparatus and methods of copending U.S. patent application Ser. No. 09/966,497, pages 27-51 and Ser. No. 09/966,450, pages 57-63 advantageously enable the production of such dosage forms according to this invention.

It is one object of this invention to provide a dosage form in which at least one active ingredient contained therein exhibits a modified release profile upon contacting of the dosage form with a liquid medium. It is another object of this invention to provide a dosage form in which the surface area for dissolution of at least one active ingredient contained therein is controlled by a partial coating. Other objects features and advantages of the invention will be apparent to those skilled in the art from the detailed description set forth below.

SUMMARY OF THE INVENTION

In one embodiment, the dosage form of this invention comprises: (a) at least one active ingredient; (b) a core having a first surface portion upon which resides an first coating and a second surface portion which is substantially free of the first coating; and (c) a shell which resides upon at least the second surface portion, wherein the shell comprises a different material from the first coating.

In another embodiment, the core comprises a cavity therein such that at least part of the second surface portion of the core is located within the cavity, and the shell resides upon at least a part of the second surface portion of the core which is located within the cavity.

In another embodiment, the cavity is an aperture which extends entirely through the core such that the aperture provides the second surface portion of the core.

In another embodiment, the shell resides upon at least part of both the first coating and the second surface portion of the core.

In another embodiment, the shell resides over all the first coating and the second surface of the core.

In another embodiment, the shell comprises a material selected from water soluble or water swellable thermoplastic film formers, water soluble or water swellable thickeners, crystallizable and non-crystallizable carbohydrates.

In another embodiment, the core is in the shape of a truncated cone.

In another embodiment, the dosage form of this invention comprises: (a) at least one active ingredient; (b) a core comprising (i) a center portion having an exterior surface and (ii) an annular portion having an exterior surface and an interior surface, wherein the annular portion interior surface is in contact with at least portion of the center portion exterior surface, and an first coating resides on at least a portion of the annular portion exterior surface; and (c) a shell which resides upon at least a portion of the exterior surface of the center portion, wherein the shell comprises a different material from the first coating.

In another embodiment, the core comprises at least one active ingredient.

In another embodiment, the center portion of the core comprises at least one active ingredient.

In another embodiment, the annular portion of the core comprises at least one active ingredient.

In another embodiment, the center portion of the core comprises a first active ingredient and the annular portion of the core comprises a second active ingredient.

In another embodiment, the shell comprises at least one active ingredient.

In another embodiment, both the shell and the core each comprise at least one active ingredient.

In another embodiment, the first coating resides upon the entire annular portion exterior surface.

In another embodiment, the shell resides upon the entire first coating and the center portion surface.

In another embodiment, the shell comprises a material selected from water soluble or water swellable thermoplastic film formers, water soluble or water swellable thickeners, crystallizable and non-crystallizable carbohydrates.

In another embodiment, the core annular portion has the shape of a torus.

In yet another embodiment, the dosage form of this invention comprises: (a) at least one active ingredient; (b) a core having an outer surface and a cavity which extends at least partially through the core such that the core outer surface has at least a first opening therein; (c) a first coating which resides on at least a portion of the core outer surface, wherein the first shell portion comprises a different material from the first coating; and (d) a first shell portion which is adjacent to the first opening and covers at least the first opening.

In another embodiment, the cavity extends entirely through the core such that the core has first and second openings therein, the first shell portion is adjacent to and covers at least the first opening, and the dosage form additionally comprises a second shell portion which is adjacent to and covers at least the second opening, wherein the first and second shell portions each comprise a material different from the first coating.

In another embodiment, the core has the shape of a torus.

In another embodiment, the first shell portion comprises at least one water soluble material.

In another embodiment, the second shell portion comprises at least one water soluble material.

In another embodiment, the first and second shell portions each comprise at least one water soluble material.

In another embodiment, the first shell portion or the core or a combination thereof comprises at least one active ingredient.

In another embodiment, the first shell portion, second shell portion or the core or a combination thereof comprises at least one active ingredient.

In another embodiment, the first shell portion resides upon at least a portion of the first coating.

In another embodiment, the shell resides upon the entire outer surface of the first coating.

In another embodiment, at least a portion of the active ingredient is released in a sustained manner.

In another embodiment, the dosage form releases at least a portion of the active ingredient at a substantially constant rate.

In another embodiment, the release of at least one active ingredient from the center portion of the core meets USP specifications for immediate release tablets containing the particular active ingredient employed.

In another embodiment, the center portion of the core provides a time delay to the release of active ingredient from the annular portion of the core.

In another embodiment, the core functions as an eroding matrix.

In another embodiment, the core functions as a diffusional matrix.

In another embodiment, the core comprises a release-modifying excipient selected from the group consisting of swellable erodible hydrophillic materials, insoluble edible materials, pH-dependent polymers, and mixtures thereof.

In another embodiment, the first coating comprises at least about 30 weight percent of a thermal reversible carrier, based on the weight of the first coating.

In another embodiment, the first coating comprises at lease about 10 weight percent of a film former selected from the group consisting of film-forming water soluble polymers, film-forming proteins, film-forming water insoluble polymers, and film-forming pH-dependent polymers.

In another embodiment, the film-former for making the core or shell or portion thereof by molding may be selected from cellulose acetate, ammonio methacrylate copolymer type B, shellac, hydroxypropylmethylcellulose, and polyethylene oxide, and combinations thereof.

In another embodiment, the shell or shell portion comprises thermoplastic polyalkalene glycols, thermoplastic polyalkalene oxides, and combinations thereof.

In another embodiment, the shell portion is breached or dissolved within 30 minutes in 900 ml water or 0.1 N HCl, or phosphate buffer solution at 37° C. with stirring by a USP type 2 (Paddle method) at 50 or 100 rpm.

In another embodiment, the release of at least one active ingredient follows a double pulse profile.

In another embodiment, the release of at least one active ingredient follows a delayed then sustained release profile.

In another embodiment, release of a first portion of active ingredient from the dosage form meets USP specifications for immediate release tablets containing the particular active ingredient employed, and release of a second portion of active ingredient from the dosage form follows a sustained, prolonged, extended, or retarded release profile.

In another embodiment, the immediately released first portion of active ingredient is contained in the shell, and the sustained release second portion of active ingredient is contained in the core.

In another embodiment, the release of one or more active ingredients follows a zero-order, first-order, or square root of time profile.

In another embodiment, the shell is substantially free of pores in the diameter range of 0.5 to 5.0 microns.

In yet another embodiment, this invention provides a method of applying a partial coating to a core in a dosage form by thermal cycle molding.

In yet another embodiment, this invention provides a method of applying a partial coating to a core in a dosage form by thermal setting molding.

In yet another embodiment, the first coating comprises up to about 55 weight percent of a release-modifying excipient selected from water-insoluble polymers and low-melting hydrophobic materials and combinations thereof.

In yet another embodiment, the release-modifying excipeint is a polycaprolactone.

DETAILED DESCRIPTION OF THE INVENTION

Figure 1A:
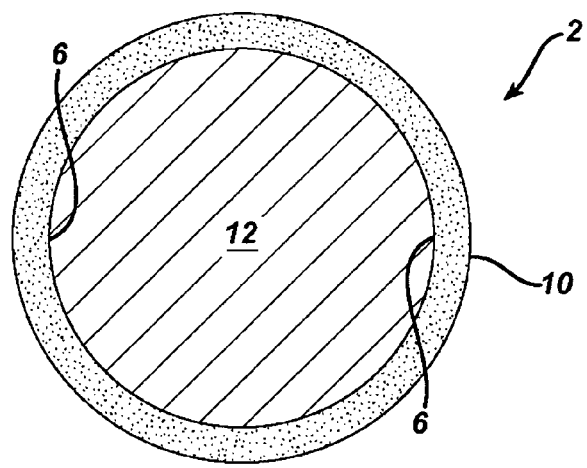
FIGS. 1A and 1B depict overhead and side views of one embodiment of the dosage form of this invention.

As used herein, the term "dosage form" applies to any solid object, semi-solid, or liquid composition designed to contain a specific pre-determined amount (i.e. dose) of a certain ingredient, for example an active ingredient as defined below. Suitable dosage forms may be pharmaceutical drug delivery systems, including those for oral administration, buccal administration, rectal administration, topical or mucosal delivery, or subcutaneous implants, or other implanted drug delivery systems; or compositions for delivering minerals, vitamins and other nutraceuticals, oral care agents, flavorants, and the like. Preferably the dosage forms of the present invention are considered to be solid, however they may contain liquid or semi-solid components. In a particularly preferred embodiment, the dosage form is an orally administered system for delivering a pharmaceutical active ingredient to the gastro-intestinal tract of a human.

The dosage forms of the present invention contain one or more active ingredients which are released therefrom upon contact of the dosage form with a liquid medium, for example a dissolution medium. Examples of suitable dissolution media for the dosage form of the invention include gastrointestinal fluids for embodiments in which the dosage form is orally ingested, mucosal fluids for embodiments in which the dosage form is for buccal delivery, intracellular fluids for embodiments in which the dosage form is an implant, moisture in the soil for embodiments in which the dosage form delivers a fertilizer or plant nutrient, and synthetic dissolution media, e.g. water or aqueous buffer solutions, for testing the performance of the dosage form in vitro.

"Water soluble," as used herein in connection with non-polymeric materials, shall mean from sparingly soluble to very soluble, i.e., not more than 100 parts water required to dissolve 1 part of the non-polymeric, water soluble solute. See Remington, *The Science and Practice of Pharmacy*, pp 208-209 (2000). "Water soluble," as used herein in connection with polymeric materials, shall mean that the polymer swells in water and can be dispersed at the molecular level to form a homogeneous dispersion or colloidal "solution."

The dosage forms of the invention exhibit modified release of one or more active ingredients contained therein. One or more active ingredients may be found in any portion of the dosage form, for example one or more active ingredients may be found within the core, the center portion, the shell portion, or coated or uncoated particles distributed therethrough. As used herein, the term "modified release" shall apply to dosage forms, matrices, particles, coatings, portions thereof, or compositions that alter the release of an active ingredient in any manner. Types of modified release include controlled, prolonged, sustained, extended, delayed, pulsatile, repeat action, and the like. Suitable mechanisms for achieving these types of modified release include diffusion, erosion, surface area control via geometry and/or impermeable barriers, or other mechanisms known in the art. Moreover, the modified release properties of the dosage form may be achieved through design of the core or a portion thereof, or the first coating, or the shell portion, or a combination of two or more of these parts of the dosage form.

In certain particularly preferred embodiments of this invention, the dosage form releases one or more active ingredients contained therein in a controlled manner, e.g. in a sustained, extended, prolonged, or retarded manner, more preferably at a substantially constant rate upon contacting of the dosage form with a liquid medium. In such embodiments, the core or center portion or shell or a portion thereof may function as a diffusional matrix or an eroding matrix.

The dosage form of the invention comprises a first coating which resides upon a first surface portion of the core. In certain embodiments, the first coating may function as a barrier to prevent release therethrough of an active ingredient contained in the underlying core portion. In such embodiments, active ingredient is typically released from a portion of the core which is not covered by the barrier coating portion. Such embodiments advantageously allow for control of the surface area for release of the active ingredient. In certain particular embodiments, for example, the surface area for release of active ingredient can be maintained substantially constant over time In certain other particular embodiments, for example, the surface area for release of active ingredient can increase over time during the dissolution period of the dosage form. The surface area for release of active ingredient may be controlled by a combination of the size of the uncoated area on the core surface, and the overall shape of the core. In certain such embodiments, the barrier coating preferably comprises a water insoluble material such as for example a water insoluble polymer. Since surface area is one factor in the dissolution equation, controlling surface area for drug release advantageously enables a further degree of control over the release rate of the drug from the dosage form. In a particularly preferred embodiment, the release of at least one active ingredient follows substantially zero-order kinetics.

The dosage form also comprises a shell or shell portion that resides on (i.e., directly contacts) or covers (i.e., shields or screens but does not necessarily directly contact) at least a portion of the exterior surface of the core where no first coating is present. The shell may reside on or cover the entire portion of the core free of first coating. Alternately the shell may reside on only a portion of the uncoated core surface. Additionally, the shell may cover all, none, or a portion of the first coating as well. In a particularly preferred embodiment the shell resides upon only the portion of the core free of first coating, and does not contact the first coating. In another embodiment, the shell covers the entire portion of the core free of first coating, and connects with the first coating at an interface, but does not substantially cover the first coating. In yet another embodiment, the shell covers both the entire portion of the core free of first coating and the entire first coating. The shell comprises a material that is different from the first coating.

In certain embodiments in which the shell comprises the overall outer surface of the dosage form, the shell is preferably of a smooth overall shape, e.g. a spheroid, ellypsoid, or other easily swallowable shape such as those having rounded edges. Accordingly, the dosage form resists damage during transport and handling and is easy to swallow, despite the shape of the core inside.

Figure 1B:
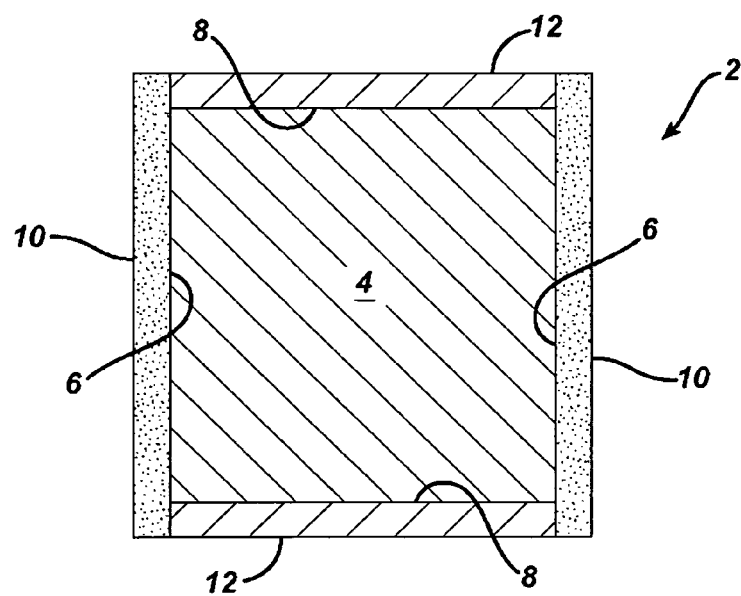

A first embodiment of this invention is depicted in FIGS. 1A and 1B. FIG. 1A depicts an overhead view and FIG. 1B depicts a side view of a dosage form 2 which comprises a core 4 having a first surface portion 6 and second surface portions 8. A first coating 10 resides upon the first surface portion 6 of core 4. However, the second surface portion 8 of core 4 is substantially free of first coating 10. A shell 12 resides upon the second surface portion 8 of core 4.

Figure 2A:
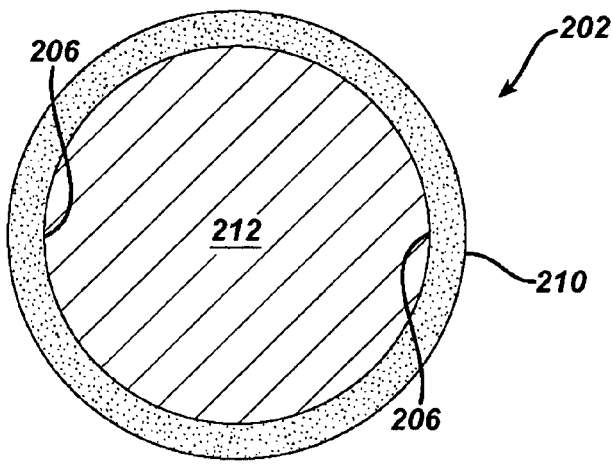
FIGS. 2A and 2B depict overhead and side views of another embodiment of the dosage form of this invention.
Figure 2B:
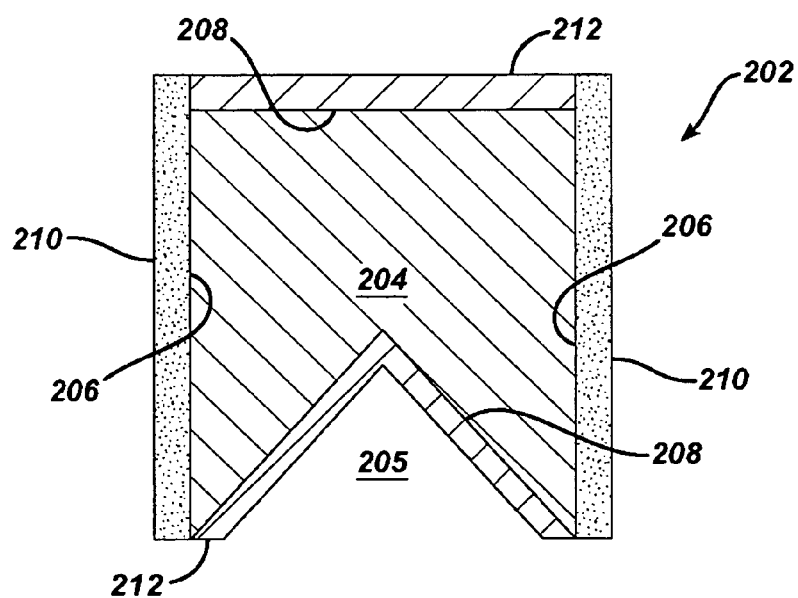

Optionally, core 4 of the dosage form depicted in FIGS. 1A and 1B may contain a cavity as shown in FIGS. 2A and 2B, which respectively depict overhead and side views of a dosage form 202 which comprises a core 204 having a first surface portion 206, a cavity 205 and a second surface portion 208. A first coating 210 resides upon the first surface portion 206 of core 204. The second surface portion 208 of core 204 is defined at least in part by cavity 205 and the second surface portion 208 is substantially free of first coating 210. A shell 212 resides upon the second surface portion 208 of core 204.

Figure 3A:
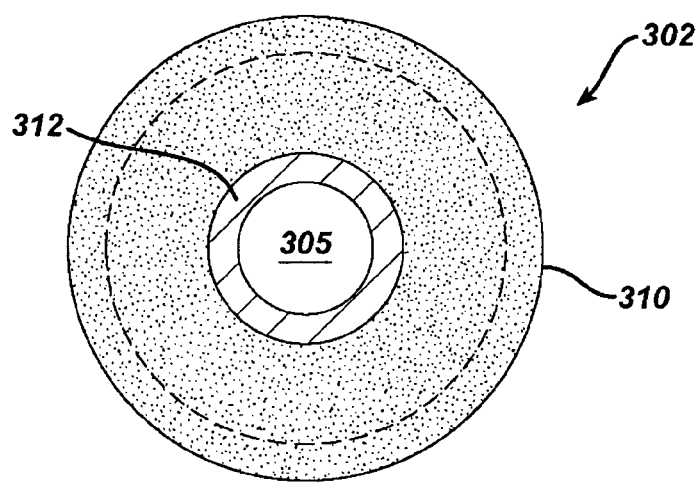
FIGS. 3A and 3B depict overhead and side views of another embodiment of the dosage form of this invention.
Figure 3B:
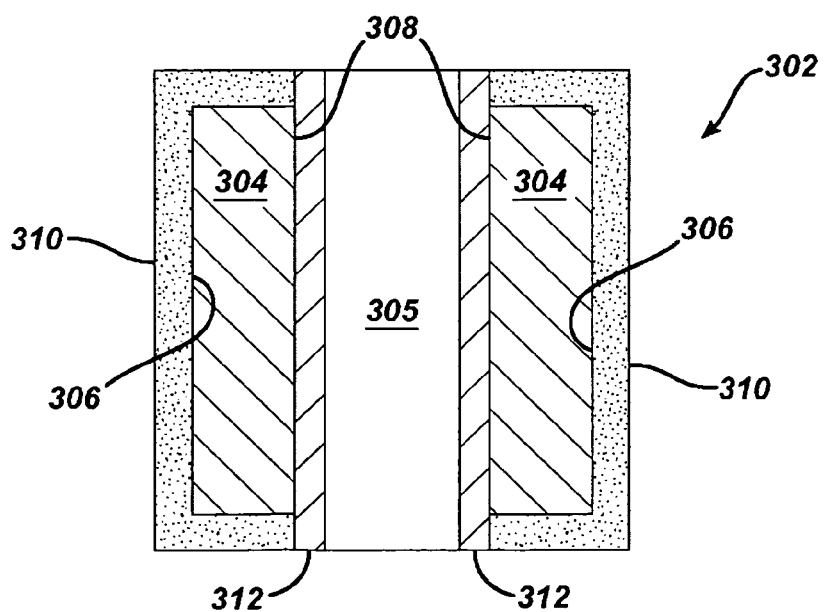

Another embodiment of this invention is depicted in FIGS. 3A and 3B, which depict a further variation of the dosage form of FIGS. 1A and 1B. FIGS. 3A and 3B depict overhead and side views of a dosage form 302 which comprises a core 304 having a first surface portion 306, an aperture 305 which extends completely through core 304 and a second surface portion 308. The second surface portion 308 of core 304 is defined by aperture 305. A first coating 310 resides upon the first surface portion 306 of core 304. Again, the second surface portion 308 is substantially free of first coating 310. A shell 312 resides upon the second surface portion 308 of core 304.

Figure 4A:
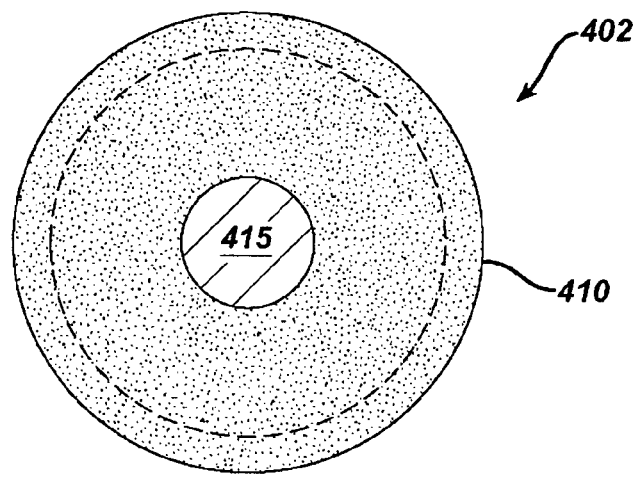
FIGS. 4A and 4B depict overhead and side views of another embodiment of the dosage form of this invention.
Figure 4B:
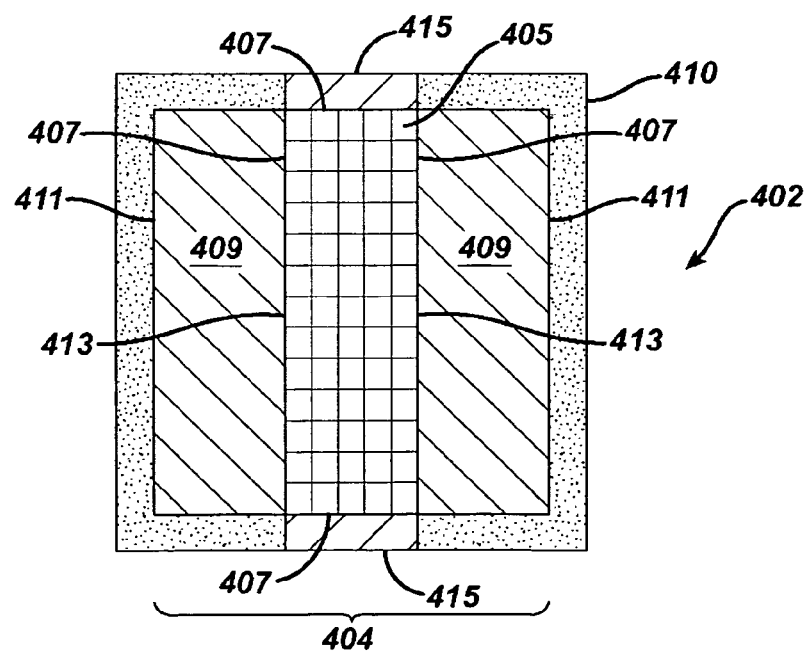

Another embodiment of this invention is depicted in FIGS. 4A and 4B, which depict overhead and side views of dosage form 402, which comprises a core 404 made up of a center portion 405 surrounded by an annular portion 409. The center portion 405 has a surface 407, while the annular portion 409 has an exterior surface 411 and an interior surface 413. The annular portion interior surface 413 is in contact with a portion of the center portion surface 407. The annular portion exterior surface 410 is covered by a first coating 410. A shell, divided into first and second shell portions 415 reside upon a portion of the center portion surface 407

Figure 5A:
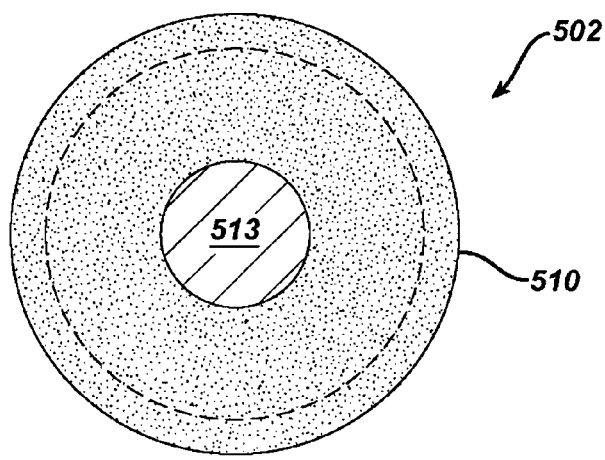
FIGS. 5A and 5B depict overhead and side views of another embodiment of the dosage form of this invention.
Figure 5B:
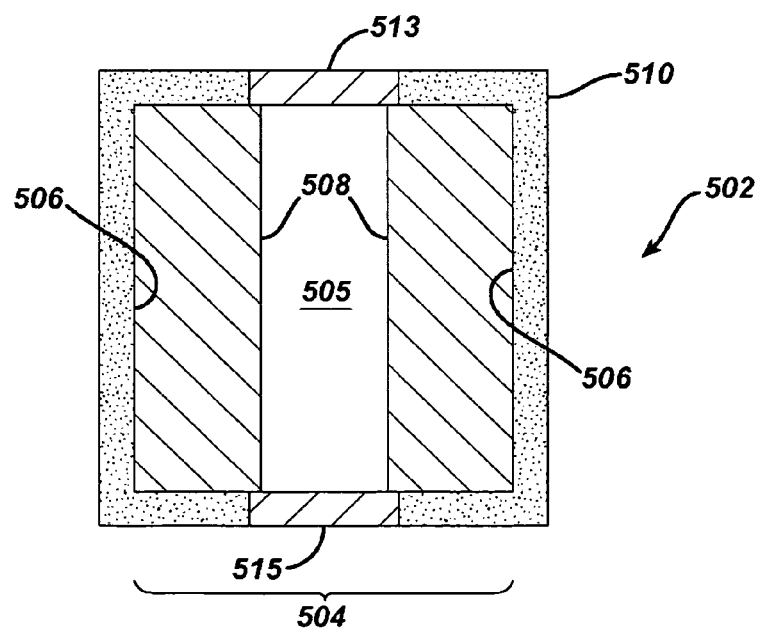

Another embodiment of this invention is depicted in FIGS. 5A and 5B, which depict overhead and side views of dosage form 502 which comprises a core 504 having an outer surface 506 and an inner surface 508 that is defined by an aperture 505 extending completely through the core 504. A first coating 510 resides upon the outer surface 506 of core 504. The inner surface 508 is substantially free of first coating 510. A first shell portion 513 covers one end of the aperture 505, and a second shell portion 515 covers the opposite end of the aperture 505. Accordingly, a void is created inside the dosage form.

Figure 7A:
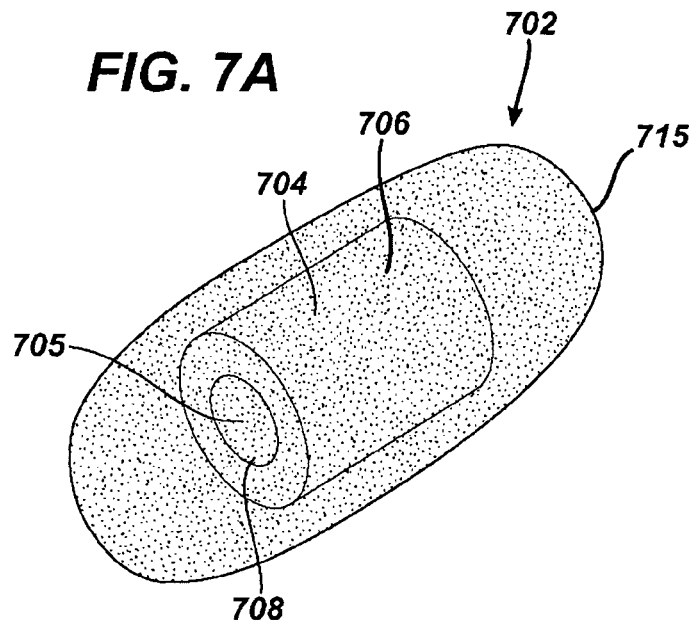
FIGS. 7A and 7B depict another embodiment of a dosage form according to the invention.
Figure 7B:
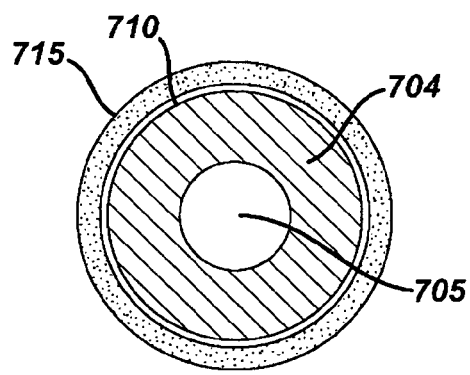

FIG. 7A depicts another embodiment of the invention. In this embodiment, the dosage form 702 comprises a core 704 having the shape of a torus. This shape has been found to be especially conducive to controlled release of an active ingredient. The core 704 has an outer surface 706 and an inner surface 708 that is defined by an aperture 705. A first coating 710 resides on the outer surface 706 of the core 704, as shown in FIG. 7B. The inner surface 708 is substantially free of first coating 710. A shell 715 encloses the entire core 704 and first coating 710. The shell 715 has a generally elliptical shape.

Suitable active ingredients for use in this invention include for example pharmaceuticals, minerals, vitamins and other nutraceuticals, oral care agents, flavorants and mixtures thereof. Suitable pharmaceuticals include analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, contraceptives, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof.

Suitable oral care agents include breath fresheners, tooth whiteners, antimicrobial agents, tooth mineralizers, tooth decay inhibitors, topical anesthetics, mucoprotectants, and the like.

Suitable flavorants include menthol, peppermint, mint flavors, fruit flavors, chocolate, vanilla, bubblegum flavors, coffee flavors, liqueur flavors and combinations and the like.

Examples of suitable gastrointestinal agents include antacids such as calcium carbonate, magnesium hydroxide, magnesium oxide, magnesium carbonate, aluminum hydroxide, sodium bicarbonate, dihydroxyaluminum sodium carbonate; stimulant laxatives, such as bisacodyl, cascara sagrada, danthron, senna, phenolphthalein, aloe, castor oil, ricinoleic acid, and dehydrocholic acid, and mixtures thereof; H2 receptor antagonists, such as famotadine, ranitidine, cimetadine, nizatidine; proton pump inhibitors such as omeprazole or lansoprazole; gastrointestinal cytoprotectives, such as sucraflate and misoprostol; gastrointestinal prokinetics, such as prucalopride, antibiotics for *H. pylori*, such as clarithromycin, amoxicillin, tetracycline, and metronidazole; antidiarrheals, such as diphenoxylate and loperamide; glycopyrrolate; antiemetics, such as ondansetron, analgesics, such as mesalamine.

In one embodiment of the invention, the active agent may be selected from bisacodyl, famotadine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment, the active agent is selected from analgesics, anti-inflammatories, and antipyretics, e.g. nonsteroidal anti-inflammatory drugs (NSAIDs), including propionic acid derivatives, e.g. ibuprofen, naproxen, ketoprofen and the like; acetic acid derivatives, e.g. indomethacin, diclofenac, sulindac, tolmetin, and the like; fenamic acid derivatives, e.g. mefanamic acid, meclofenamic acid, flufenamic acid, and the like; biphenylcarbodylic acid derivatives, e.g. diflunisal, flufenisal, and the like; and oxicams, e.g. piroxicam, sudoxicam, isoxicam, meloxicam, and the like. In a particularly preferred embodiment, the active agent is selected from propionic acid derivative NSAIDs, e.g. ibuprofen, naproxen, flurbiprofen, fenbufen, fenoprofen, indoprofen, ketoprofen, fluprofen, pirprofen, carprofen, oxaprozin, pranoprofen, suprofen, and pharmaceutically acceptable salts, derivatives, and combinations thereof. In a particular embodiment of the invention, the active agent may be selected from acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof.

In another embodiment of the invention, the active agent may be selected from pseudoephedrine, phenylpropanolamine, chlorpheniramine, dextromethorphan, diphenhydramine, astemizole, terfenadine, fexofenadine, loratadine, desloratidine, doxilamine, norastemizole, cetirizine, mixtures thereof and pharmaceutically acceptable salts, esters, isomers, and mixtures thereof.

Examples of suitable polydimethylsiloxanes, which include, but are not limited to dimethicone and simethicone, are those disclosed in U.S. Pat. Nos. 4,906,478, 5,275,822, and 6,103,260. As used herein, the term "simethicone" refers to the broader class of polydimethylsiloxanes, including but not limited to simethicone and dimethicone.

The active ingredient or ingredients are present in the dosage form in a therapeutically effective amount, which is an amount that produces the desired therapeutic response upon oral administration and can be readily determined by one skilled in the art. In determining such amounts, the particular active ingredient being administered, the bioavailability characteristics of the active ingredient, the dose regime, the age and weight of the patient, and other factors must be considered, as known in the art. Preferably, the dosage form comprises at least about 85 weight percent of the active ingredient. In one preferred embodiment, the core comprises at least about 85 weight percent of the active ingredient.

The active ingredient or ingredients may be present in the dosage form in any form. For example, the active ingredient may be dispersed at the molecular level, e.g. melted or dissolved, within the dosage form, or may be in the form of particles, which in turn may be coated or uncoated. If the active ingredient is in form of particles, the particles (whether coated or uncoated) typically have an average particle size of about 1-2000 microns. In one preferred embodiment, such particles are crystals having an average particle size of about 1-300 microns. In another preferred embodiment, the particles are granules or pellets having an average particle size of about 50-2000 microns, preferably about 50-1000 microns, most preferably about 100-800 microns.

In embodiments where an active ingredient is contained within the core, at least a portion of the active ingredient may be optionally coated with a release-modifying coating, as known in the art. This advantageously provides an additional tool for modifying the release profile of the dosage form. In particular embodiments of this invention in which coated particles are employed, the particles may be as described herein, and the particles may be coated using conventional coating technology which is well known to those skilled in the art including microencapsulation techniques such as coacervation, spray-drying, and fluidized bed coating including tangential spray rotor coating and bottom spray wurster coating. Examples of suitable particle coating methods and materials can be found in U.S. Pat. Nos. 5,286,497; 4,863,742; 4,173,626; 4,980,170; 4,984,240; 5,912,013; 6,270,805; and 6,322,819.

In embodiments in which it is desired for the active ingredient to be absorbed into the systemic circulation of an animal, the active ingredient or ingredients are preferably capable of dissolution upon contact with a fluid such as water, gastric fluid, intestinal fluid or the like. In one embodiment, the dissolution characteristics of at least one active ingredient meets USP specifications for immediate release tablets containing the active ingredient. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19-20 and 856 (1999). In embodiments in which at least one active ingredient is released immediately, the immediately released active ingredient is preferably contained in the shell or on the surface of the shell, e.g. in a further coating surrounding at least a portion of the shell. In another embodiment, the dissolution characteristics of one or more active ingredients are modified: e.g. controlled, sustained, extended, retarded, prolonged, delayed and the like. In a preferred embodiment in which one or more active ingredients are released in a modified manner, the modified release active or actives are preferably contained in the core.

The core of the present invention may be prepared by any suitable method, including for example compression and molding, and depending on the method by which it is made, typically comprises, in addition to the active ingredient, a variety of excipients (inactive ingredients which may be useful for conferring desired physical properties to the dosage form).

Figure 6:
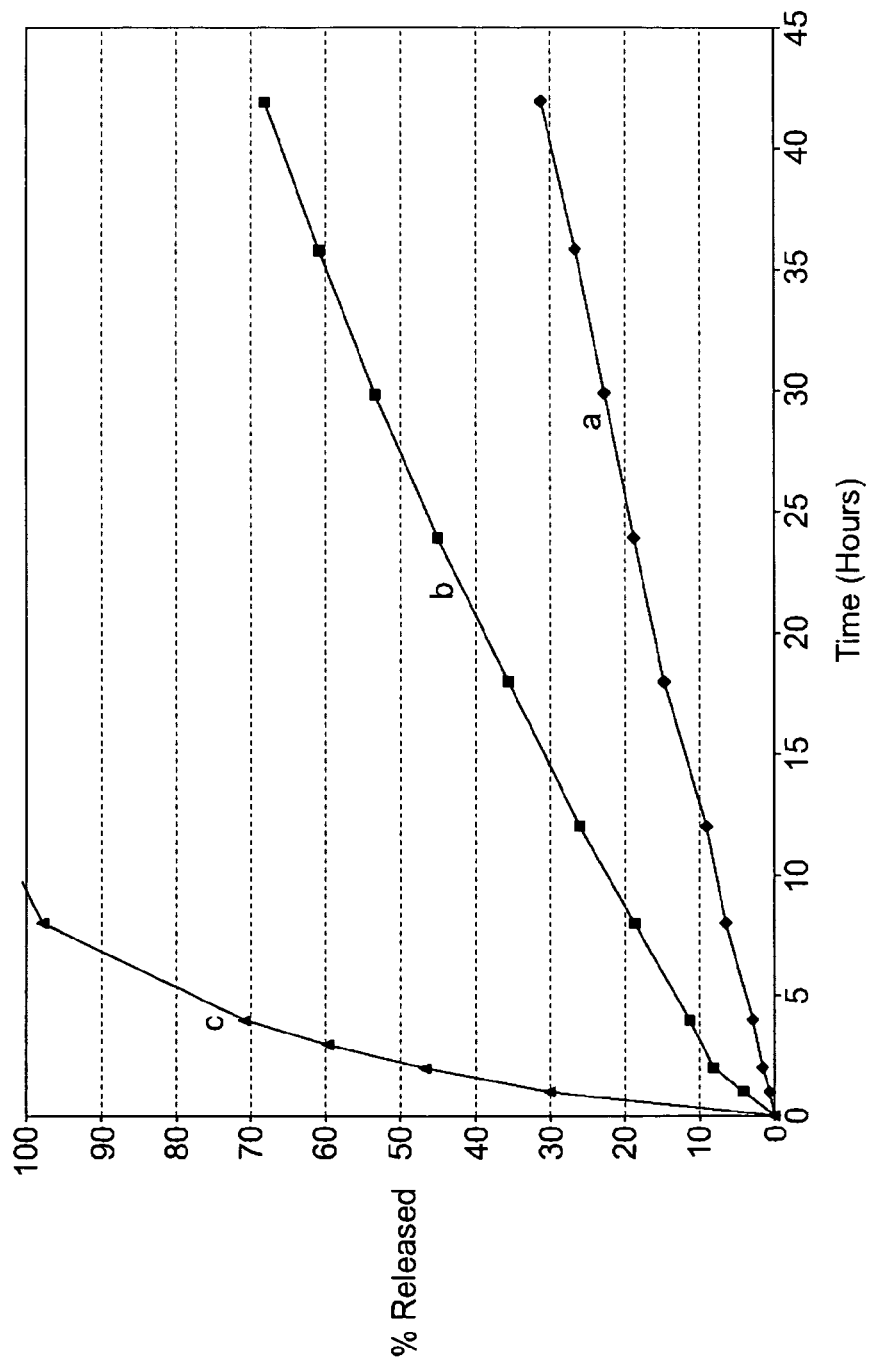
FIG. 6 depicts the % release of active ingredient vs. hours measured for the dosage form of Example 1.

In a preferred embodiment, the core is prepared by the compression methods and apparatus described in copending U.S. patent application Ser. No. 09/966,509, pages 16-27, the disclosure of which is incorporated herein by reference. Specifically, the core is made using a rotary compression module comprising a fill zone, insertion zone, compression zone, ejection zone, and purge zone in a single apparatus having a double row die construction as shown in FIG. 6 of U.S. patent application Ser. No. 09/966,509. The dies of the compression module are preferably filled using the assistance of a vacuum, with filters located in or near each die. The purge zone of the compression module includes an optional powder recovery system to recover excess powder from the filters and return excess powder to the dies.

In embodiments in which the core, or a portion thereof, is made by compression, suitable excipients include fillers, binders, disintegrants, lubricants, glidants, and the like, as known in the art. In embodiments in which the core is made by compression, the core may further comprise a release-modifying compressible excipient.

Suitable fillers for use in making the core, or a portion thereof, by compression include water-soluble compressible carbohydrates such as sugars, which include dextrose, sucrose, maltose, and lactose, sugar-alcohols, which include mannitol, sorbitol, maltitol, xylitol, starch hydrolysates, which include dextrins, and maltodextrins, and the like, water insoluble plastically deforming materials such as microcrystalline cellulose or other cellulosic derivatives, water-insoluble brittle fracture materials such as dicalcium phosphate, tricalcium phosphate and the like and mixtures thereof.

Suitable binders for making the core, or a portion thereof, by compression include dry binders such as polyvinyl pyrrolidone, hydroxypropylmethylcellulose, and the like; wet binders such as water-soluble polymers, including hydrocolloids such as acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, polyvinyl pyrrolidone, cellulosics, sucrose, starches, and the like; and derivatives and mixtures thereof.

Suitable disintegrants for making the core, or a portion thereof, by compression, include sodium starch glycolate, cross-linked polyvinylpyrrolidone, cross-linked carboxymethylcellulose, starches, microcrystalline cellulose, and the like.

Suitable lubricants for making the core, or a portion thereof, by compression include long chain fatty acids and their salts, such as magnesium stearate and stearic acid, talc, glycerides and waxes.

Suitable glidants for making the core, or a portion thereof, by compression, include colloidal silicon dioxide, and the like.

Suitable release-modifying compressible excipients for making the core, or a portion thereof, by compression include swellable erodible hydrophillic materials, insoluble edible materials, pH-dependent polymers, and mixtures thereof.

Suitable swellable erodible hydrophilic materials for use as release-modifying excipients for making the core, or a portion thereof, by compression include: water swellable cellulose derivatives, polyalkalene glycols, thermoplastic polyalkalene oxides, acrylic polymers, hydrocolloids, clays, gelling starches, and swelling cross-linked polymers, and derivitives, copolymers, and combinations thereof. Examples of suitable water swellable cellulose derivatives include sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, hydroxypropylethylcellulose. Examples of suitable polyalkalene glycols include polyethylene glycol. Examples of suitable thermoplastic polyalkalene oxides include poly (ethylene oxide). Examples of suitable acrylic polymers include potassium methacrylate-divinylbenzene copolymer, polymethylmethacrylate, CARBOPOL (high-molecular weight cross-linked acrylic acid homopolymers and copolymers), and the like. Examples of suitable hydrocolloids include alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan. Examples of suitable clays include smectites such as bentonite, kaolin, and laponite; magnesium trisilicate, magnesium aluminum silicate, and the like, and derivatives and mixtures thereof. Examples of suitable gelling starches include acid hydrolyzed starches, swelling starches such as sodium starch glycolate, and derivatives thereof. Examples of suitable swelling cross-linked polymers include cross-linked polyvinyl pyrrolidone, cross-linked agar, and cross-linked carboxymethylcellose sodium.

Suitable insoluble edible materials for use as release-modifying excipients for making the core, or a portion thereof, by compression include water-insoluble polymers, and low-melting hydrophobic materials. Examples of suitable water-insoluble polymers include ethylcellulose, polyvinyl alcohols, polyvinyl acetate, polycaprolactones, cellulose acetate and its derivatives, acrylates, methacrylates, acrylic acid copolymers; and the like and derivatives, copolymers, and combinations thereof. Suitable low-melting hydrophobic materials include fats, fatty acid esters, phospholipids, and waxes. Examples of suitable fats include hydrogenated vegetable oils such as for example cocoa butter, hydrogenated palm kernel oil, hydrogenated cottonseed oil, hydrogenated sunflower oil, and hydrogenated soybean oil; and free fatty acids and their salts. Examples of suitable fatty acid esters include sucrose fatty acid esters, mono, di, and triglycerides, glyceryl behenate, glyceryl palmitostearate, glyceryl monostearate, glyceryl tristearate, glyceryl trilaurylate, glyceryl myristate, GlycoWax-932, lauroyl macrogol-32 glycerides, and stearoyl macrogol-32 glycerides. Examples of suitable phospholipids include phosphotidyl choline, phosphotidyl serene, phosphotidyl enositol, and phosphotidic acid. Examples of suitable waxes include carnauba wax, spermaceti wax, beeswax, candelilla wax, shellac wax, microcrystalline wax, and paraffin wax; fat-containing mixtures such as chocolate; and the like.

Suitable pH-dependent polymers for use as release-modifying excipients for making the core, or a portion thereof, by compression include enteric cellulose derivatives, for example hydroxypropyl methylcellulose phthalate, hydroxypropyl methylcellulose acetate succinate, cellulose acetate phthalate; natural resins such as shellac and zein; enteric acetate derivatives such as for example polyvinylacetate phthalate, cellulose acetate phthalate, acetaldehyde dimethylcellulose acetate; and enteric acrylate derivatives such as for example polymethacrylate-based polymers such as poly(methacrylic acid, methyl methacrylate) 1:2, which is commercially available from Rohm Pharma GmbH under the tradename EUDRAGIT S, and poly(methacrylic acid, methyl methacrylate) 1:1, which is commercially available from Rohm Pharma GmbH under the tradename EUDRAGIT L; and the like, and derivatives, salts, copolymers, and combinations thereof.

Suitable pharmaceutically acceptable adjuvants for making the core, or a portion thereof, by compression include, preservatives; high intensity sweeteners such as aspartame, acesulfame potassium, sucralose, and saccharin; flavorants; colorants; antioxidants; surfactants; wetting agents; and the like and mixtures thereof.

The core or a portion thereof may also be formed by molding, using either a solvent free, or solvent based method.

In another embodiment, the core is prepared by thermal setting molding using the method and apparatus described in copending U.S. patent application Ser. No. 09/966,450, pages 57-63, the disclosure of which is incorporated herein by reference. In this embodiment, the core is formed by injecting a starting material in flowable form into a molding chamber. The starting material preferably comprises an active ingredient and a thermal setting material at a temperature above the melting point of the thermal setting material but below the decomposition temperature of the active ingredient. The starting material is cooled and solidifies in the molding chamber into a shaped form (i.e., having the shape of the mold).

In another embodiment, the core is prepared by thermal cycle molding using the method and apparatus described in copending U.S. patent application Ser. No. 09/966,497, pages 27-51, the disclosure of which is incorporated herein by reference. In this embodiment, the core is formed by injecting a starting material in flowable form into a heated molding chamber. The starting material preferably comprises an active ingredient and a thermoplastic material at a temperature above the set temperature of the thermoplastic material but below the decomposition temperature of the active ingredient. The starting material is cooled and solidifies in the molding chamber into a shaped form (i.e., having the shape of the mold).

The first coating may be applied to the core by known methods, such as dipping, or spraying. In a preferred embodiment, however, the first coating is applied to the core by molding. The first coating may be molded using a solvent free or solvent based method, preferably using either the thermal cycling molding module, or thermal setting molding module, as described herein. This invention advantageously achieves a cost effective process for applying a partial coating to selected portions of a core without the need for costly and complex subsequent steps of previously known methods, such as application of a complete coating to a core, followed by removal of a portion of the core and coating to permit selective application of another coating to a portion of the core.

In certain embodiments of the invention, the first coating may function as a barrier to the passage of water or active ingredient therethrough. In certain other embodiments, the first coating may function as a semi-permeable membrane, allowing water or solvent to pass into the core, but being impermeable to dissolved active ingredient, thereby preventing the passage of active ingredient therethrough. In certain other embodiments, the first coating may function as a diffusional membrane, allowing the passage of active ingredient therethrough at a rate controlled by the thickness, porosity and tortuosity of the first coating. In certain other embodiments, the first coating may function as an erosional coating to provide a time delay to the release of one or more portions of active ingredient in the core. In certain other embodiments, the first coating may comprise one or more active ingredients. In one embodiment in which the first coating comprises active ingredient, the first coating may comprise a water soluble active ingredient intended for immediate release from the dosage form, which dissolves promptly upon contact of the dosage form with a liquid medium, thereby creating pores in the first coating for the diffusion of a second dose of active ingredient contained in the core or a portion thereof.

The first coating preferably comprises from about 10 to about 100 weight percent of a film former. In embodiments in which the first coating functions as a barrier, the film former is preferably a water insoluble material such as for example a water insoluble polymer. In embodiments in which the first coating functions as a semipermeable membrane, allowing water or solvent to pass into the core, but being impermeable to dissolved active ingredient, thereby preventing the passage of active ingredient therethrough, the film former is preferably selected from water insoluble polymers, pH-dependent polymers, water soluble polymers, and combinations thereof. In embodiments in which the first coating may function as a diffusional membrane, allowing the passage of active ingredient therethrough at a rate controlled by the thickness, porosity and tortuosity of the first coating, the film former is preferably selected from water insoluble polymers, pH-dependent polymers, and combinations thereof, and the first coating preferably further comprises a pore former. In embodiments in which the first coating functions as a delayed release coating to delay release of a portion of active ingredient which is contained in the core or a portion thereof, first coating preferably further comprises a swellable erodible hydrophilic material.

The shell or shell portion of the present invention is preferably applied by molding, such as thermal cycle or thermal setting molding, as described herein, using either a solvent free or solvent based method. The method of the invention advantageously enables a partial shell to be applied to or deposited upon a selected area of the core and optionally the first coating.

The shell comprises a material that is compositionally different from the first coating. As used herein, the term "compositionally different" means having features that are readily distinguishable by qualitative or quantitative chemical analysis, physical testing, or visual observation. For example, the first coating and shell materials may contain different ingredients, or different levels of the same ingredients, or the first and second materials may have different physical or chemical properties, different functional properties, or be visually distinct. Examples of physical or chemical properties that may be different include hydrophylicity, hydrophobicity, hygroscopicity, elasticity, plasticity, tensile strength, crystallinity, and density. Examples of functional properties which may be different include rate and/or extent of dissolution of the material itself or of an active ingredient therefrom, rate of disintegration of the material, permeability to active ingredients, permeability to water or aqueous media, and the like. Examples of visual distinctions include size, shape, topography, or other geometric features, color, hue, opacity, and gloss.

For example the first coating and shell may comprise different types or levels of colorants, opacifiers, film-formers, etc. Alternatively, the first coating and shell may have different thickness. The first coating and shell may have different functionalities. For example, the first coating and shell may confer different release properties to an active ingredient contained in either the subject coating or shell, or in a corresponding underlying core portion. In one particular embodiment, the first coating may function as a barrier to the passage therethrough of one or more active ingredients contained in the underlying core portion; and the shell may function as an eroding matrix from which active ingredient dispersed in the shell or shell portion is liberated by the dissolution of successive layers of the shell portion surface.

In certain preferred embodiments of the invention, the core, or the first coating, or the shell, or a portion thereof, is prepared by molding. In such embodiments, the core, or the shell, or a portion thereof, comprises a flowable material. The flowable material may be any edible material that is flowable at a temperature between about 37° C. and 250° C., and that is solid, semi-solid, or can form a gel at a temperature between about −10° C. and about 35° C. When it is in the fluid or flowable state, the flowable material may comprise a dissolved or molten component, and optionally a solvent such as for example water or organic solvents, or combinations thereof. The solvent may be partially or substantially removed by drying.

Suitable flowable materials for making the core, or the first coating or the shell, or a portion thereof by molding include those comprising thermoplastic materials; film formers; thickeners such as gelling polymers or hydrocolloids; low melting hydrophobic materials such as fats and waxes; non-crystallizable carbohydrates; and the like. Suitable molten components of the flowable material include thermoplastic materials, low melting hydrophobic materials, and the like. Suitable dissolved components for the flowable material include film formers, thickeners such as gelling polymers or hydrocolloids, non-crystallizable carbohydrates, and the like.

Suitable thermoplastic materials can be molded and shaped when heated, and include both water soluble and water insoluble polymers that are generally linear, not crosslinked, nor strongly hydrogen bonded to adjacent polymer chains. Examples of suitable thermoplastic materials include: thermoplastic water swellable cellulose derivatives, thermoplastic water insoluble cellulose derivatives, thermoplastic vinyl polymers, thermoplastic starches, thermoplastic polyalkalene glycols, thermoplastic polyalkalene oxides, and amorphous sugar-glass, and the like, and derivatives, copolymers, and combinations thereof. Examples of suitable thermoplastic water swellable cellulose derivatives include hydroxypropyl cellulose (HPC), hydroxypropylmethyl cellulose (HPMC), methyl cellulose (MC). Examples of suitable thermoplastic water insoluble cellulose derivatives include cellulose acetate (CA), ethyl cellulose (EC), cellulose acetate butyrate (CAB), cellulose propionate. Examples of suitable thermoplastic vinyl polymers include polyvinyl alcohol (PVA) and polyvinyl pyrrolidone (PVP). Examples of suitable thermoplastic starches include those disclosed in U.S. Pat. No. 5,427,614, which is incorporated herein by reference. Examples of suitable thermoplastic polyalkalene glycols include polyethylene glycol; Examples of suitable thermoplastic polyalkalene oxides include polyethylene oxide having a molecular weight from about 100,000 to about 900,000 Daltons. Other suitable thermoplastic materials include sugar in the form on an amorphous glass such as that used to make hard candy forms.

Any film former known in the art is suitable for use in the flowable material of the present invention. Examples of suitable film formers include, but are not limited to, film-forming water soluble polymers, film-forming proteins, film-forming water insoluble polymers, and film-forming pH-dependent polymers. In one embodiment, the film-former for making the core or shell or portion thereof by molding may be selected from cellulose acetate, ammonio methacrylate copolymer type B, shellac, hydroxypropylmethylcellulose, and polyethylene oxide, and combinations thereof.

Suitable film-forming water soluble polymers include water soluble vinyl polymers such as polyvinylalcohol (PVA); water soluble polycarbohydrates such as hydroxypropyl starch, hydroxyethyl starch, pullulan, methylethyl starch, carboxymethyl starch, pre-gelatinized starches, and film-forming modified starches; water swellable cellulose derivatives such as hydroxypropyl cellulose (HPC), hydroxypropylmethyl cellulose (HPMC), methyl cellulose (MC), hydroxyethylmethylcellulose (HEMC), hydroxybutylmethylcellulose (HBMC), hydroxyethylethylcellulose (HEEC), and hydroxyethylhydroxypropylmethyl cellulose (HEMPMC); water soluble copolymers such as methacrylic acid and methacrylate ester copolymers, polyvinyl alcohol and polyethylene glycol copolymers, polyethylene oxide and polyvinylpyrrolidone copolymers; and derivatives and combinations thereof.

Suitable film-forming proteins may be natural or chemically modified, and include gelatin, whey protein, myofibrillar proteins, coaggulatable proteins such as albumin, casein, caseinates and casein isolates, soy protein and soy protein isolates, zein; and polymers, derivatives and mixtures thereof.

Suitable film-forming water insoluble polymers, include for example ethylcellulose, polyvinyl alcohols, polyvinyl acetate, polycaprolactones, cellulose acetate and its derivatives, acrylates, methacrylates, acrylic acid copolymers; and the like and derivatives, copolymers, and combinations thereof.

Suitable film-forming pH-dependent polymers include enteric cellulose derivatives, such as for example hydroxypropyl methylcellulose phthalate, hydroxypropyl methylcellulose acetate succinate, cellulose acetate phthalate; natural resins, such as shellac and zein; enteric acetate derivatives such as for example polyvinylacetate phthalate, cellulose acetate phthalate, acetaldehyde dimethylcellulose acetate; and enteric acrylate derivatives such as for example polymethacrylate-based polymers such as poly(methacrylic acid, methyl methacrylate) 1:2, which is commercially available from Rohm Pharma GmbH under the tradename EUDRAGIT S, and poly(methacrylic acid, methyl methacrylate) 1:1, which is commercially available from Rohm Pharma GmbH under the tradename EUDRAGIT L; and the like, and derivatives, salts, copolymers, and combinations thereof.

One suitable hydroxypropylmethylcellulose compound for use as a thermoplastic film-forming water soluble polymer is HPMC 2910, which is a cellulose ether having a degree of substitution of about 1.9 and a hydroxypropyl molar substitution of 0.23, and containing, based upon the total weight of the compound, from about 29% to about 30% methoxyl groups and from about 7% to about 12% hydroxylpropyl groups. HPMC 2910 is commercially available from the Dow Chemical Company under the tradename METHOCEL E. METHOCEL E5, which is one grade of HPMC-2910 suitable for use in the present invention, has a viscosity of about 4 to 6 cps (4 to 6 millipascal-seconds) at 20° C. in a 2% aqueous solution as determined by a Ubbelohde viscometer. Similarly, METHOCEL E6; which is another grade of HPMC-2910 suitable for use in the present invention, has a viscosity of about 5 to 7 cps (5 to 7 millipascal-seconds) at 20° C. in a 2% aqueous solution as determined by a Ubbelohde viscometer. METHOCEL E15, which is another grade of HPMC-2910 suitable for use in the present invention, has a viscosity of about 15000 cps (15 millipascal-seconds) at 20° C. in a 2% aqueous solution as determined by a ubbelohde viscometer. As used herein, "degree of substitution" shall mean the average number of substituent groups attached to a anhydroglucose ring, and "hydroxypropyl molar substitution" shall mean the number of moles of hydroxypropyl per mole anhydroglucose.

One suitable polyvinyl alcohol and polyethylene glycol copolymer is commercially available from BASF Corporation under the tradename KOLLICOAT IR.

As used herein, "modified starches" include starches that have been modified by crosslinking, chemically modified for improved stability or optimized performance, or physically modified for improved solubility properties or optimized performance. Examples of chemically-modified starches are well known in the art and typically include those starches that have been chemically treated to cause replacement of some of its hydroxyl groups with either ester or ether groups. Crosslinking, as used herein, may occur in modified starches when two hydroxyl groups on neighboring starch molecules are chemically linked. As used herein, "pre-gelatinized starches" or "instantized starches" refers to modified starches that have been pre-wetted, then dried to enhance their coldwater solubility. Suitable modified starches are commercially available from several suppliers such as, for example, A.E. Staley Manufacturing Company, and National Starch & Chemical Company. One suitable film forming modified starch includes the pre-gelatinized waxy maize derivative starches that are commercially available from National Starch & Chemical Company under the tradenames PURITY GUM and FILMSET, and derivatives, copolymers, and mixtures thereof. Such waxy maize starches typically contain, based upon the total weight of the starch, from about 0 percent to about 18 percent of amylose and from about 100% to about 88% of amylopectin.

Another suitable film forming modified starch includes the hydroxypropylated starches, in which some of the hydroxyl groups of the starch have been etherified with hydroxypropyl groups, usually via treatment with propylene oxide. One example of a suitable hydroxypropyl starch that possesses film-forming properties is available from Grain Processing Company under the tradename, PURE-COTE B790.

Suitable tapioca dextrins for use as film formers include those available from National Starch & Chemical Company under the tradenames CRYSTAL GUM or K-4484, and derivatives thereof such as modified food starch derived from tapioca, which is available from National Starch and Chemical under the tradename PURITY GUM 40, and copolymers and mixtures thereof.

Any thickener known in the art is suitable for use in the flowable material of the present invention. Examples of such thickeners include but are not limited to hydrocolloids (also referred to herein as gelling polymers), clays, gelling starches, and crystallizable carbohydrates, and derivatives, copolymers and mixtures thereof.

Examples of suitable hydrocolloids (also referred to herein as gelling polymers) such as alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, pectin, whelan, rhamsan, zooglan, methylan, chitin, cyclodextrin, chitosan. Examples of suitable clays include smectites such as bentonite, kaolin, and laponite; magnesium trisilicate, magnesium aluminum silicate, and the like, and derivatives and mixtures thereof. Examples of suitable gelling starches include acid hydrolyzed starches, and derivatives and mixtures thereof. Additional suitable thickening hydrocolloids include low-moisture polymer solutions such as mixtures of gelatin and other hydrocolloids at water contents up to about 30%, such as for example those used to make "gummi" confection forms.

Additional suitable thickeners include crystallizable carbohydrates, and the like, and derivatives and combinations thereof. Suitable crystallizable carbohydrates include the monosaccharides and the oligosaccharides. Of the monosaccharides, the aldohexoses e.g., the D and L isomers of allose, altrose, glucose, mannose, gulose, idose, galactose, talose, and the ketohexoses e.g., the D and L isomers of fructose and sorbose along with their hydrogenated analogs: e.g., glucitol (sorbitol), and mannitol are preferred. Of the oligosaccharides, the 1,2-disaccharides sucrose and trehalose, the 1,4-disaccharides maltose, lactose, and cellobiose, and the 1,6-disaccharides gentiobiose and melibiose, as well as the trisaccharide raffinose are preferred along with the isomerized form of sucrose known as isomaltulose and its hydrogenated analog isomalt. Other hydrogenated forms of reducing disaccharides (such as maltose and lactose), for example, maltitol and lactitol are also preferred. Additionally, the hydrogenated forms of the aldopentoses: e.g., D and L ribose, arabinose, xylose, and lyxose and the hydrogenated forms of the aldotetroses: e.g., D and L erythrose and threose are preferred and are exemplified by xylitol and erythritol, respectively.

In one embodiment of the invention, the flowable material comprises gelatin as a gelling polymer. Gelatin is a natural, thermogelling polymer. It is a tasteless and colorless mixture of derived proteins of the albuminous class which is ordinarily soluble in warm water. Two types of gelatin—Type A and Type B—are commonly used. Type A gelatin is a derivative of acid-treated raw materials. Type B gelatin is a derivative of alkali-treated raw materials. The moisture content of gelatin, as well as its Bloom strength, composition and original gelatin processing conditions, determine its transition temperature between liquid and solid. Bloom is a standard measure of the strength of a gelatin gel, and is roughly correlated with molecular weight. Bloom is defined as the weight in grams required to move a half-inch diameter plastic plunger 4 mm into a 6.67% gelatin gel that has been held at 10° C. for 17 hours. In a preferred embodiment, the flowable material is an aqueous solution comprising 20% 275 Bloom pork skin gelatin, 20% 250 Bloom Bone Gelatin, and approximately 60% water.

Suitable xanthan gums include those available from C.P. Kelco Company under the tradenames KELTROL 1000, XANTROL 180, or K9B310.

Suitable clays include smectites such as bentonite, kaolin, and laponite; magnesium trisilicate, magnesium aluminum silicate, and the like, and derivatives and mixtures thereof.

"Acid-hydrolyzed starch," as used herein, is one type of modified starch that results from treating a starch suspension with dilute acid at a temperature below the gelatinization point of the starch. During the acid hydrolysis, the granular form of the starch is maintained in the starch suspension, and the hydrolysis reaction is ended by neutralization, filtration and drying once the desired degree of hydrolysis is reached. As a result, the average molecular size of the starch polymers is reduced. Acid-hydrolyzed starches (also known as "thin boiling starches") tend to have a much lower hot viscosity than the same native starch as well as a strong tendency to gel when cooled.

"Gelling starches," as used herein, include those starches that, when combined with water and heated to a temperature sufficient to form a solution, thereafter form a gel upon cooling to a temperature below the gelation point of the starch. Examples of gelling starches include, but are not limited to, acid hydrolyzed starches such as that available from Grain Processing Corporation under the tradename PURE-SET B950; hydroxypropyl distarch phosphate such as that available from Grain Processing Corporation under the tradename, PURE-GEL B990, and mixtures thereof.

Suitable low-melting hydrophobic materials include fats, fatty acid esters, phospholipids, and waxes. Examples of suitable fats include hydrogenated vegetable oils such as for example cocoa butter, hydrogenated palrn kernel oil, hydrogenated cottonseed oil, hydrogenated sunflower oil, and hydrogenated soybean oil; and free fatty acids and their salts. Examples of suitable fatty acid esters include sucrose fatty acid esters, mono, di, and triglycerides, glyceryl behenate, glyceryl palmitostearate, glyceryl monostearate, glyceryl tristearate, glyceryl trilaurylate, glyceryl myristate, Glyco-Wax-932, lauroyl macrogol-32 glycerides, and stearoyl macrogol-32 glycerides. Examples of suitable phospholipids include phosphotidyl choline, phosphotidyl serene, phosphotidyl enositol, and phosphotidic acid. Examples of suitable waxes include carnauba wax, spermaceti wax, beeswax, candelilla wax, shellac wax, microcrystalline wax, and paraffin wax; fat-containing mixtures such as chocolate; and the like.

Suitable non-crystallizable carbohydrates include non-crystallizable sugars such as polydextrose, and starch hydrolysates, e.g. glucose syrup, corn syrup, and high fructose corn syrup; and non-crystallizable sugar-alcohols such as maltitol syrup.

Suitable solvents for optional use as components of the flowable material include water; polar organic solvents such as methanol, ethanol, isopropanol, acetone, and the like; and non-polar organic solvents such as methylene chloride, cyclohexane, and the like; and mixtures thereof.

The flowable material may optionally comprise adjuvants or excipients, which may comprise up to about 30% by weight of the flowable material. Examples of suitable adjuvants or excipients include plasticizers, detackifiers, humectants, surfactants, anti-foaming agents, colorants, flavorants, sweeteners, opacifiers, and the like. Suitable plasticizers for making the core, the shell, or a portion thereof, by molding include, but not be limited to polyethylene glycol; propylene glycol; glycerin; sorbitol; triethyl citrate; tribuyl citrate; dibutyl sebecate; vegetable oils such as castor oil, rape oil, olive oil, and sesame oil; surfactants such as polysorbates, sodium lauryl sulfates, and dioctyl-sodium sulfosuccinates; mono acetate of glycerol; diacetate of glycerol; triacetate of glycerol; natural gums; triacetin; acetyltributyl citrate; diethyloxalate; diethylmalate; diethyl fumarate; diethylmalonate; dioctylphthalate; dibutylsuccinate; glyceroltributyrate; hydrogenated castor oil; fatty acids; substituted triglycerides and glycerides; and the like and/or mixtures thereof. In one embodiment, the plasticizer is triethyl citrate. In certain embodiments, the shell is substantially free of plasticizers, i.e. contains less than about 1%, say less than about 0.01% of plasticizers.

In one preferred embodiment, the flowable material comprises less than 5% humectants, or alternately is substantially free of humectants, such as glycerin, sorbitol, maltitol, xylitol, or propylene glycol. Humectants have traditionally been included in pre-formed films employed in enrobing processes, such as that disclosed in U.S. Pat. Nos. 5,146,730 and 5,459,983, to ensure adequate flexibility or plasticity and bondability of the film during processing. Humectants function by binding water and retaining it in the film. Pre-formed films used in enrobing processes can typically comprise up to 45% water. Disadvantageously, the presence of humectant prolongs the drying process, and can adversely affect the stability of the finished dosage form.

In certain particularly preferred embodiments of the invention, the core, or the first coating, or the shell, or portions thereof may be molded using a solvent-free process. In certain such embodiments, the core, or the first coating, or the shell, or portions thereof may comprise active ingredient contained within a molded excipient matrix. In other such embodiments, the core, or the first coating, or the shell, or portions thereof may comprise a molded excipient matrix substantially free of active ingredient. The molded matrix typically comprises at least about 30 weight percent of a thermal-reversible carrier. The molded matrix may optionally further comprise up to about 55 weight percent of one or more release-modifying moldable excipients as described below, and optionally up to about 30 weight percent of various adjuvants such as for example plasticizers, gelling agents, colorants, stabilizers, preservatives, and the like as known in the art.

In certain other particularly preferred embodiments of the invention, the core or the first coating or the shell or a portion or portions thereof are prepared using a solvent-based molding process, the molded core or coating or shell or portion will typically comprise at least about 10 weight percent, e.g. at least about 12 weight percent or at least about 15 weight percent or at least about 20 weight percent or at least about 25 weight percent of a film-former. Here, the solvent-molded shell portion or portions may optionally further comprise up to about 55 weight percent of a release-modifying excipient. The solvent-molded shell portion or portions may again also optionally further comprise up to about 30 weight percent total of various plasticizers, adjuvants, and excipients.

In certain embodiments in which one or more active ingredients contained in the core are released from the dosage form in a controlled marner, the core, or a portion thereof may function as a diffusional matrix. In these embodiments, the core or core portion preferably comprises active ingredient, distributed throughout an insoluble porous matrix, which contains pores or channels through which fluids can enter the core or core portion, and the active ingredient must diffuse in order to be released from the dosage form. In these embodiments, the rate of active ingredient release from the core portion will depend upon the area (A) of the matrix, the diffusion coefficient (D), the porosity (E) and tortuosity (T) of the matrix, the drug solubility (Cs) in the dissolution medium, and the drug concentration (Cp) in the dosage form. In preferred embodiments in which a core portion functions as a diffusional matrix, the release of the active ingredient from the core or core portion may be described as controlled, prolonged, sustained, or extended. In these embodiments, the contribution to active ingredient dissolution from the subject core portion may follow zero-order, first-order, or preferably square-root of time kinetics. In these embodiments, the core may be made by compression or molding. In embodiments in which the core or portion thereof functions as a diffusional matrix through which active ingredient contained therein is liberated in a sustained, extended, prolonged, or retarded manner, the core or core portion preferably comprises a release-modifying excipient selected from combinations of insoluble edible materials and pore formers. Alternately, in such embodiments in which the core or core portion is prepared by solvent-free molding, the thermal-reversible carrier may function by dissolving and forming pores or channels through which the active ingredient may be liberated.

In certain other embodiments in which one or more active ingredients contained in the core are released from the dosage form in a controlled manner, the core or portion thereof may function as an eroding matrix from which active ingredient dispersed in the core or core portion is liberated by the dissolution of successive layers of the core or core portion surface. In these embodiments, the rate of active ingredient release will depend on the dissolution rate of the matrix material in the core or core portion. Particularly useful matrix materials for providing surface erosion include those that first absorb liquid, then swell and/or gel prior to dissolving. In embodiments in which the core or portion thereof functions as an eroding matrix from which dispersed active ingredient is liberated in a sustained, extended, prolonged, or retarded manner, the core or core portion may be made by compression or by molding, and the core or core portion preferably comprises a release-modifying excipient selected from swellable erodible hydrophilic materials, pH-dependent polymers, insoluble edible materials, and combinations thereof. In certain particular such embodiments, the eroding matrix core or core portion preferably comprises a swellable erodible hydrophilic material.

In certain preferred embodiments of the invention, one or more shell portions contain active ingredient which is released essentially immediately upon ingestion of the dosage form. In these embodiments, the shell portion preferably comprises materials which exhibit rapid dissolution in gastrointestinal fluids.

In certain other embodiments, one or more shell portions function as a diffusional membrane which contains pores through which fluids can enter the dosage form, and dissolved active ingredient can be released. In these embodiments, the rate of release of active ingredient from an underlying core portion will depend upon the total pore area in the shell portion, the pathlength of the pores, and the solubility and diffusivity of the active ingredient (in addition to its rate of release from the core portion itself). In preferred embodiments in which a shell portion functions as a diffusional membrane, the release of the active ingredient from the dosage form may be described as controlled, prolonged, sustained or extended. In these embodiments, the contribution to active ingredient dissolution from the subject shell portion may follow zero-order, first-order, or square-root of time kinetics. In certain such embodiments, the diffusional membrane shell portion preferably comprises a pore former and an insoluble material such as for example a film forming water insoluble polymer.

In certain other embodiments, one or more shell portions function as an eroding matrix from which active ingredient dispersed in the shell portion is liberated by the dissolution of successive layers of the shell portion surface. In these embodiments, the rate of active ingredient release will depend on the dissolution rate of the matrix material in the shell portion. Particularly useful matrix materials for providing surface erosion include those which first absorb liquid, then swell and/or gel prior to dissolving. In certain such embodiments, the eroding matrix shell portion preferably comprises a swellable erodible hydrophilic material.

In certain other embodiments, one or more shell portions function as a barrier to prevent release therethrough of an active ingredient contained in the underlying core or first coating. In such embodiments, active ingredient is typically released from a portion of the dosage form which is not covered by the barrier shell portion. Such embodiments advantageously allow for further control of the surface area for release of the active ingredient. In certain such embodiments, the barrier shell portion preferably comprises a water insoluble material such as for example a water insoluble polymer.

In certain other embodiments, one or more shell portions function as a delayed release coating to delay release of an active ingredient which is contained in the core or a portion thereof. In these embodiments, the lag-time for onset of active ingredient release may be governed by erosion of the coating or diffusion through the coating or a combination thereof. In certain such embodiments, the eroding matrix shell portion preferably comprises a swellable erodible hydrophilic material.

In embodiments in which the first coating, the shell, or a portion thereof function to modify the release of an active ingredient which is contained in the core or the subject coating or shell portion, the thickness of the coating or shell portion is critical to the release properties of the dosage form. Advantageously the dosage forms of the invention can be made with precise control over coating and shell thickness. In a preferred embodiment in which the first coating or shell portions function to modify the release of an active ingredient which is contained in the core or the subject coating or shell portion, the first coating or shell portion or portions are made by the thermal cycle or thermal setting molding methods described herein.

Suitable thermal-reversible carriers for making the core, or the first coating, or the shell, or a portion thereof, by molding are thermoplastic materials typically having a melting point below about 110° C., more preferably between about 20 and about 100° C. Examples of suitable thermal-reversible carriers for solvent-free molding include thermoplastic polyalkalene glycols, thermoplastic polyalkalene oxides, low melting hydrophobic materials, thermoplastic polymers, thermoplastic starches, and the like. Preferred thermal-reversible carriers include polyethylene glycol and polyethylene oxide. Suitable thermoplastic polyalkylene glycols for use as thermal-reversible carriers include polyethylene glycol having molecular weight from about 100 to about 20,000, e.g. from about 1000 to about 8,000 Daltons. Suitable thermoplastic polyalkalene oxides include polyethylene oxide having a molecular weight from about 100,000 to about 900,000 Daltons. Suitable low-melting hydrophobic materials for use as thermal-reversible carriers include fats, fatty acid esters, phospholipids, and waxes which are solid at room temperature, fat-containing mixtures such as chocolate; and the like. Examples of suitable fats include hydrogenated vegetable oils such as for example cocoa butter, hydrogenated palm kernel oil, hydrogenated cottonseed oil, hydrogenated sunflower oil, and hydrogenated soybean oil; and free fatty acids and their salts. Examples of suitable fatty acid esters include sucrose fatty acid esters, mono, di, and triglycerides, glyceryl behenate, glyceryl palmitostearate, glyceryl monostearate, glyceryl tristearate, glyceryl trilaurylate, glyceryl myristate, Glyco-Wax-932, lauroyl macrogol-32 glycerides, and stearoyl macrogol-32 glycerides. Examples of suitable phospholipids include phosphotidyl choline, phosphotidyl serine, phosphotidyl enositol, and phosphotidic acid. Examples of suitable waxes which are solid at room temperature include carnauba wax, spermaceti wax, beeswax, candelilla wax, shellac wax, microcrystalline wax, and paraffin wax. Suitable thermoplastic polymers for use as thermal-reversible carriers include thermoplastic water swellable cellulose derivatives, thermoplastic water insoluble polymers, thermoplastic vinyl polymers, thermoplastic starches, and thermoplastic resins, and combinations thereof. Suitable thermoplastic water swellable cellulose derivatives include include hydroxypropylmethyl cellulose (HPMC), methyl cellulose (MC), carboxymethylcellulose (CMC), cross-linked hydroxypropylcellulose, hydroxypropyl cellulose (HPC), hydroxybutylcellulose (HBC), hydroxyethylcellulose (HEC), hydroxypropylethylcellulose, hydroxypropylbutylcellulose, hydroxypropylethylcellulose, and salts, derivatives, copolymers, and combinations thereof. Suitable thermoplastic water insoluble polymers include ethylcellulose, polyvinyl alcohols, polyvinyl acetate, polycaprolactones, cellulose acetate and its derivatives, acrylates, methacrylates, acrylic acid copolymers, and the like and derivatives, copolymers, and combinations thereof. Suitable thermoplastic vinyl polymers include polyvinylacetate, polyvinyl alcohol, and polyvinyl pyrrolidone (PVP). Examples of suitable thermoplastic starches for use as thermal-reversible carriers include those disclosed in U.S. Pat. No. 5,427,614, which is incorporated herein by reference. Examples of suitable thermoplastic resins for use as thermal-reversible carriers include dammars, mastic, rosin, shellac, sandarac, and glycerol ester of rosin. In one embodiment, the thermal-reversible carrier for making the core, or a portion thereof, by molding is selected from polyalkylene glycols, polyalkaline oxides, and combinations thereof.

Suitable release-modifying excipients for making the core, or the shell, or a portion thereof, by solvent free or solvent based molding include but are not limited to swellable erodible hydrophilic materials, pH-dependent polymers, pore formers, and insoluble edible materials. In one embodiment, suitable release-modifying excipients for making the core, or the shell, or a portion thereof, by molding include hydroxypropylmethylcellulose, polyethylene oxide, ammonio methacrylate copolymer type B, and shellac, and combinations thereof.

Suitable swellable erodible hydrophilic materials for use as release-modifying excipients for making the core, or the shell, or a portion thereof by a solvent-free molding process include water swellable cellulose derivatives, polyalkalene glycols, thermoplastic polyalkalene oxides, acrylic polymers, hydrocolloids, clays, gelling starches, and swelling cross-linked polymers, and derivitives, copolymers, and combinations thereof. Examples of suitable water swellable cellulose derivatives include sodium carboxymethylcellulose, cross-inked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, hydroxypropylethylcellulose. Examples of suitable polyalkalene glyclols include polyethylene glycol. Examples of suitable thermoplastic polyalkalene oxides include poly (ethylene oxide). Examples of suitable acrylic polymers include potassium methacrylatedivinylbenzene copolymer, polymethylmethacrylate, CARBOPOL (high-molceular weight cross-linked acrylic acid homopolymers and copolymers), and the like. Examples of suitable hydrocolloids include alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan. Examples of suitable clays include smectites such as bentonite, kaolin, and laponite; magnesium trisilicate, magnesium aluminum silicate, and the like, and derivatives and mixtures thereof. Examples of suitable gelling starches include acid hydrolyzed starches, swelling starches such as sodium starch glycolate, and derivatives thereof. Examples of suitable swelling cross-linked polymers include cross-linked polyvinyl pyrrolidone, cross-linked agar, and cross-linked carboxymethylcellose sodium.

Suitable pH-dependent polymers for use as release-modifying moldable excipients for making the molded matrix or molded core or molded shell or a portion thereof by molding include enteric cellulose derivatives, for example hydroxypropyl methylcellulose phthalate, hydroxypropyl methylcellulose acetate succinate, cellulose acetate phthalate; natural resins such as shellac and zein; enteric acetate derivatives such as for example polyvinylacetate phthalate, cellulose acetate phthalate, acetaldehyde dimethylcellulose acetate; and enteric acrylate derivatives such as for example polymethacrylate-based polymers such as poly(methacrylic acid, methyl methacrylate) 1:2, which is commercially available from Rohm Pharma GmbH under the tradename EUDRAGIT S, and poly(methacrylic acid, methyl methacrylate) 1:1, which is commercially available from Rohm Pharma GmbH under the tradename EUDRAGIT L; and the like, and derivatives, salts, copolymers, and combinations thereof.

Suitable insoluble edible materials for use as release-modifying excipients making the core, or the shell, or a portion thereof by molding, include water-insoluble polymers, and low-melting hydrophobic materials. Examples of suitable water-insoluble polymers include ethylcellulose, polyvinyl alcohols, polyvinyl acetate, polycaprolactones, cellulose acetate and its derivatives, acrylates, methacrylates, acrylic acid copolymers; and the like and derivatives, copolymers, and combinations thereof. Suitable low-melting hydrophobic materials include fats, fatty acid esters, phospholipids, and waxes. Examples of suitable fats include hydrogenated vegetable oils such as for example cocoa butter, hydrogenated palm kernel oil, hydrogenated cottonseed oil, hydrogenated sunflower oil, and hydrogenated soybean oil; and free fatty acids and their salts. Examples of suitable fatty acid esters include sucrose fatty acid esters, mono, di, and triglycerides, glyceryl behenate, glyceryl palmitostearate, glyceryl monostearate, glyceryl tristearate, glyceryl trilaurylate, glyceryl myristate, GlycoWax-932, lauroyl macrogol-32 glycerides, and stearoyl macrogol-32 glycerides. Examples of suitable phospholipids include phosphotidyl choline, phosphotidyl serene, phosphotidyl enositol, and phosphotidic acid. Examples of suitable waxes include carnauba wax, spermaceti wax, beeswax, candelilla wax, shellac wax, microcrystalline wax, and paraffin wax; fat-containing mixtures such as chocolate; and the like.

Suitable pore formers for use as release-modifying excipients for making the molded matrix, the core, the shell, or a portion thereof by molding include water-soluble organic and inorganic materials. In one embodiment the pore former is hydroxypropylmethylcellulose. Examples of suitable water-soluble organic materials include water soluble polymers including water soluble cellulose derivatives such as hydroxypropylmethylcellulose, and hydroxypropylcellulose; water soluble carbohydrates such as sugars, and starches; water soluble polymers such as polyvinylpyrrolidone and polyethylene glycol, and insoluble swelling polymers such as microcrystalline cellulose. Examples of suitable water soluble inorganic materials include salts such as sodium chloride and potassium chloride and the like and/or mixtures thereof.

The core may be in a variety of different shapes. For example, the core may be shaped as a polyhedron, such as a cube, pyramid, prism, or the like; or may have the geometry of a space figure with some non-flat faces, such as a cone, truncated cone, cylinder, sphere, torus, or the like. In certain embodiments the core may have the shape of a torus, cylinder, or truncated cone. In certain embodiments, the core has one or more major faces. For example in embodiments wherein the core is a compressed tablet, the core surface typically has two opposing major faces formed by contact with the upper and lower punch faces in the compression machine. In such embodiments the core surface typically further comprises a "belly-band" located between the two major faces, and formed by contact with the die walls in the compression machine. Exemplary core shapes which may be employed include tablet shapes formed from compression tooling shapes described by "The Elizabeth Companies Tablet Design Training Manual" (Elizabeth Carbide Die Co., Inc., p. 7 (McKeesport, Pa.) (incorporated herein by reference) as follows (the tablet shape corresponds inversely to the shape of the compression tooling):

1. Shallow Concave.
2. Standard Concave.
3. Deep Concave.
4. Extra Deep Concave.
5. Modified Ball Concave.
6. Standard Concave Bisect.
7. Standard Concave Double Bisect.
8. Standard Concave European Bisect.
9. Standard Concave Partial Bisect.
10. Double Radius.
11. Bevel & Concave.
12. Flat Plain.
13. Flat-Faced-Beveled Edge (F.F.B.E.).
14. F.F.B.E. Bisect.
15. F.F.B.E. Double Bisect.
16. Ring.
17. Dimple.
18. Ellipse.
19. Oval.
20. Capsule.
21. Rectangle.
22. Square.
23. Triangle.
24. Hexagon.
25. Pentagon.
26. Octagon.
27. Diamond.
28. Arrowhead.
29. Bullet.
30. Shallow Concave.
31. Standard Concave.
32. Deep Concave.
33. Extra Deep Concave.
34. Modified Ball Concave.
35. Standard Concave Bisect.
36. Standard Concave Double Bisect.
37. Standard Concave European Bisect.
38. Standard Concave Partial Bisect.
39. Double Radius.
40. Bevel & Concave.
41. Flat Plain.
42. Flat-Faced-Beveled Edge (F.F.B.E.).
43. F.F.B.E. Bisect.
44. F.F.B.E. Double Bisect.
45. Ring.
46. Dimple.
47. Ellipse.
48. Oval.
49. Capsule.
50. Rectangle.
51. Square.
52. Triangle.
53. Hexagon.
54. Pentagon.
55. Octagon.
56. Diamond.
57. Arrowhead.
58. Bullet.
59. Barrel.
60. Half Moon.
61. Shield.
62. Heart.
63. Almond.
64. House/Home Plate.
65. Parallelogram.
66. Trapezoid.
67. FIG. 8/Bar Bell.
68. Bow Tie.
69. Uneven Triangle.

In one embodiment of the invention, the core comprises multiple portions, for example a first portion and a second portion. The portions may be prepared by the same or different methods and mated using various techniques, such as the thermal cycle molding and thermal setting molding methods described herein. For example, the first and second portions may both be made by compression, or both may be made by molding. Or one portion may be made by compression and the other by molding. The compression module of copending U.S. patent application Ser. No. 09/966,509, pp. 16-27, the disclosure of which is incorporated herein by reference, may be employed to make the compressed portion. The molded portion may be made using the thermal cycle molding module described in U.S. patent application Ser. No. 09/966,497, pp. 27-51 or the thermal setting molding module described in U.S. patent application Ser. No. 09/966,450, pp. 57-63, the disclosures of which are incorporated herein by reference. A transfer device as described in U.S. patent application Ser. No. 09/966,414, pp. 51-57, the disclosure of which is incorporated herein by reference, may be used to transfer the compressed portion of the molding module.

The same or different active ingredient may be present in the first and second portions of the core. Alternately, one or more core portions may be substantially free of active ingredients.

In embodiments wherein the shell is prepared by a solvent-free molding process, the shell typically has a thickness of about 500 to about 4000 microns. In embodiments wherein the shell or a portion thereof is prepared by a solvent-based molding process, the shell typically has a thickness of less than about 800 microns, e.g. about 100 to about 600 microns, e.g. about 150 to about 400 microns.

In certain other embodiments, the shell or a portion thereof is prepared by molding using a solvent based process. In such embodiments the solvent-molded shell typically comprises at least about 10 weight percent of a film-former. Here, the solvent-molded shell may optionally further comprise up to about 55 weight percent of a release-modifying agent. The solvent-molded shell may again also optionally further comprise up to about 30 weight percent total of various plasticizers, adjuvants and excipients.

In embodiments in which the shell is prepared by molding, either by a solvent-free process or by a solvent-based process, the shell typically is substantially free of pores in the diameter range of 0.5 to 5.0 microns, i.e. has a pore volume in the pore diameter range of 0.5 to 5.0 microns of less than about 0.02 cc/g, preferably less than about 0.01 cc/g, more preferably less than about 0.005 cc/g. Typical compressed materials have pore volumes in this diameter range of more than about 0.02 cc/g. Pore volume, pore diameter and density may be determined using a Quantachrome Instruments PoreMaster 60 mercury intrusion porosimeter and associated computer software program known as "Porowin." The procedure is documented in the Quantachrome Instruments PoreMaster Operation Manual. The PoreMaster determines both pore volume and pore diameter of a solid or powder by forced intrusion of a non-wetting liquid (mercury), which involves evacuation of the sample in a sample cell (penetrometer), filling the cell with mercury to surround the sample with mercury, applying pressure to the sample cell by: (i) compressed air (up to 50 psi maximum); and (ii) a hydraulic (oil) pressure generator (up to 60000 psi maximum). Intruded volume is measured by a change in the capacitance as mercury moves from outside the sample into its pores under applied pressure. The corresponding pore size diameter (d) at which the intrusion takes place is calculated directly from the so-called "Washburn Equation": $d=-(4\gamma(\cos\theta)/P)$ where $\gamma$ is the surface tension of liquid mercury, $\theta$ is the contact angle between mercury and the sample surface and P is the applied pressure.

Equipment used for Pore Volume Measurements:
1. Quantachrome Instruments PoreMaster 60.
2. Analytical Balance capable of weighing to 0.0001 g.
3. Desiccator.

Reagents Used for Measurements:
1. High purity nitrogen.
2. Triply distilled mercury.
3. High pressure fluid (Dila AX, available from Shell Chemical Co.).
4. Liquid nitrogen (for Hg vapor cold trap).
5. Isopropanol or methanol for cleaning sample cells.
6. Liquid detergent for cell cleaning.

Procedure:

The samples remain in sealed packages or as received in the dessicator until analysis. The vacuum pump is switched on, the mercury vapor cold trap is filled with liquid nitrogen, the compressed gas supply is regulated at 55 psi., and the instrument is turned on and allowed a warm up time of at least 30 minutes. The empty penetrometer cell is assembled as described in the instrument manual and its weight is recorded. The cell is installed in the low pressure station and "evacuation and fill only" is selected from the analysis menu, and the following settings are employed:

Fine Evacuation time: 1 min.
Fine Evacuation rate: 10
Coarse Evacuation time: 5 min.

The cell (filled with mercury) is then removed and weighed. The cell is then emptied into the mercury reservoir, and two tablets from each sample are placed in the cell and the cell is reassembled. The weight of the cell and sample are then recorded. The cell is then installed in the low-pressure station, the low-pressure option is selected from the menu, and the following parameters are set:

Mode: Low pressure
Fine evacuation rate: 10
Fine evacuation until: 200% Hg
Coarse evacuation time: 10 min.
Fill pressure: Contact+0.1
Maximum pressure: 50
Direction: Intrusion And Extrusion
Repeat: 0
Mercury contact angle: 140
Mercury surface tension: 480

Data acquisition is then begun. The pressure vs. cumulative volume-intruded plot is displayed on the screen. After low-pressure analysis is complete, the cell is removed from the low-pressure station and reweighed. The space above the mercury is filled with hydraulic oil, and the cell is assembled and installed in the high-pressure cavity. The following settings are used:

Mode: Fixed rate
Motor speed: 5
Start pressure: 20
End pressure: 60,000
Direction: Intrusion and extrusion
Repeat: 0
Oil fill length: 5
Mercury contact angle: 140
Mercury surface tension: 480

Data acquisition is then begun and graphic plot pressure vs. intruded volume is displayed on the screen. After the high pressure run is complete, the low-and high-pressure data files of the same sample are merged.

In embodiments in which the shell or a portion thereof comprises an active ingredient intended to have immediate release from the dosage form, the shell or that portion thereof is preferably prepared via the solvent-free molding method described above. In such embodiments the thermal-reversible carrier is preferably selected from polyethylene glycol with weight average molecular weight from about 1450 to about 20000, polyethylene oxide with weight average molecular weight from about 100,000 to about 900,000, and the like.

In embodiments in which the shell confers sustained, extended, or retarded release of an active ingredient contained in the shell, the release-modifying agent in the shell preferably comprises a swellable erodible hydrophilic material, and may optionally comprise a secondary gelling agent such as for example cross-linked carboxymethylcellulose, cross-linked polyvinylpyrrolidone, or sodium starch glycolate.

In a particular embodiment of this invention at least one active ingredient contained within the dosage form exhibits a delayed and sustained release profile. By "delayed then sustained release profile" it is meant that the release of that particular active ingredient from the dosage form is delayed for a pre-determined time after ingestion by the patient, and the delay period ("lag time") is followed by sustained (prolonged, extended, or retarded) release of that active ingredient. In this embodiment, the shell or shell portion provides for the delay period, and is preferably substantially free of the active ingredient to be released in a delayed then sustained manner. In such embodiments, the delayed then sustained release active ingredient is preferably contained within the corresponding underlying core portion, or optionally dispersed throughout the entire core. In such embodiments the core or core portion may function for example as an eroding matrix or a diffusional matrix, or an osmotic pump. In embodiments in which the core portion functions as a diffusional matrix through which active ingredient is liberated in a sustained, extended, prolonged, or retarded manner, the core portion preferably comprises a release-modifying excipient selected from combinations of insoluble edible materials and pore-formers. Alternately, in such embodiments in which the core portion is prepared by molding, the thermal-reversible carrier may function by dissolving and forming pores or channels through which the active ingredient may be liberated. In embodiments in which the core portion functions as an eroding matrix from which dispersed active ingredient is liberated in a sustained, extended, prolonged, or retarded manner, the core portion preferably comprises a release-modifying compressible or moldable excipient selected from swellable erodible hydrophilic materials, pH-dependent polymers, and combinations thereof.

In another particular embodiment of this invention at least one active ingredient contained within the dosage form exhibits a double pulse release profile. By "double pulse" it is meant that a first portion of active ingredient is released essentially immediately upon contacting of the dosage form with a liquid medium, followed by a delay period, followed by immediate release of a second portion of active ingredient. In such embodiments in which one or more shell portions contain active ingredient which is released essentially immediately upon ingestion of the dosage form, the shell portion preferably comprises materials which exhibit rapid dissolution in gastro-intestinal fluids. For example the immediate release shell portion or portions may comprise readily soluble materials selected from water soluble or water swellable thermoplastic film formers, water soluble or water swellable thickeners, crystallizable and non-crystallizable carbohydrates. In certain such embodiments, suitable water soluble or water swellable thermoplastic film formers may be selected from water swellable cellulose derivatives, thermoplastic starches, polyalkalene glycols, polyalkalene oxides, and amorphous sugar glass, and combinations thereof. In certain other such embodiments, suitable film formers may be selected from film forming water soluble polymers such as for example water soluble vinyl polymers, water soluble polycarbohydrates, water swellable cellulose derivatives, and water soluble copolymers; film-forming proteins, and combinations thereof. In certain other such embodiments, suitable thickeners may be selected from gelling polymers or hydrocolloids; gelling starches, and crystallizable carbohydrates. In certain other such embodiments, suitable non-crystallizable carbohydrates may be selected from polydextrose, starch hydrolysates, and non-crystallizable sugar alcohols. In such embodiments, the immediate release shell portion will preferably be breached or dissolved within 30 minutes in 900 ml water or 0.1 N HCl, or phosphate buffer solution at 37° C. with stirring by a USP type 2 (Paddle method) at 50 or 100 rpm.

This invention will be illustrated by the following examples, which are not meant to limit the invention in any way.

EXAMPLE 1

Dosage forms according to the invention were made as follows. First, cores were prepared using the following ingredients:

| Granulation | Trade Name | Manufacturer | Weight % | Mg/ Dosage Form |
|---|---|---|---|---|
| Pseudoephedrine HCl Crystal | | BASF PharmaChemikalien GmbH & Co. Ludwigshafen/ Rhein. | 15.0 | 85 |
| Polyethylene Oxide (MW 300,000) | Polyox ® WSR N-750 | Union Carbide Corporation, Danbury, CT | 75.0 | 424 |
| Hydroxypropyl Methylcellulose | Methocel E5 | The Dow Chemical Company, Midland, MI | 8.5 | 48 |
| Magnesium Stearate | | Mallinckrodt Inc., St. Louis, MO | 1.5 | 9 |
| FD&C Blue #1 | | Colorcon Inc., West Point, PA | Trace Amount | |
| Alcohol USP (dried as solvent) | | | | |

The pseudoephedrine HCl crystal, hydroxypropyl methylcellulose, polyethylene oxide and FD&C Blue #1 were mixed in a plastic bag for 1-2 minutes. This powder mixture was added to the (5 qt) bowl of a planetary mixer (Hobart Corp., Dayton, Ohio). The alcohol was added to the powder mixture while mixing at low speed. The ingredients were mixed for 10 minutes. The resulting granulation was removed from the bowl and was dried at room temperature for 12 to 16 hours to remove all residual solvent. The granulation was screened through a 20-mesh screen and put into a plastic bag. Magnesium stearate was added to the dry granules, followed by mixing for 3 minutes.

Cores were then prepared by pressing the granulation using a Manesty Beta-press (Thomas Engineering, Inc., Hoffman Estates, Ill.). A round, concave punch and die unit having 0.4455" diameter was used for compression. Granulation was fed into the cavity of the press and compressed into solid cores.

A first coating material was next prepared from the following ingredients:

| Granulation | Trade Name | Manufacturer | Weight % | Mg/ dosage Formt |
|---|---|---|---|---|
| Polycaprolactones Isopropanol (dried as solvent) | CAPA 686 | Solvay Interox, Inc., Laporte, TX | 100 | 286 |

The polycaprolactones were first added to a beaker. The isopropanol was added thereto and the combination was mixed with a spatula until a uniform dispersion was obtained.

A thermal cycle molding module as described in copending U.S. application Ser. No. 09/966,497 at pages 27-51, the disclosure of which is incorporated herein by reference, was used to apply the first coating material onto the cores. The thermal cycle molding module was a laboratory scale unit and comprised a single mold made from an upper mold assembly and a lower mold assembly. The lower mold assembly was first cycled to a cold stage at 25° C. for 30 seconds. First coating material was then introduced into a cavity in the lower mold assembly. A core as prepared above was then inserted into the same cavity. The upper mold assembly was then cycled to a cold stage at 25° C. for 30 seconds. First coating material was added to a cavity in the upper mold assembly. The lower and upper mold assemblies were mated and cycled to a hot stage at 85° C. for 1 minute, followed by cycling to a cold stage at 10° C. for 1 minute to harden the first coating. The upper and lower mold assemblies were separated and the core coated with the first coating was ejected.

The "weight gains" of the cores due to the presence of the first coating were recorded. The coated cores were dried at room temperature for 24 hours to remove all residual solvent.

Next, holes were drilled through the centers of the coated cores. 0.277 cm holes were drilled through in one set of coated cores using a ⅜" drill (model 315.10491, Sears, Roebuck and Co.) equipped with a 7/64" drill bit. 0.397-cm holes were drilled in a second set of coated cores using a ⅜" drill equipped with a 5/32" drill bit.

Finally, a shell material was prepared using the following ingredient:

| Shell | Trade Name | Manufacturer | Weight % | Mg/Dosage Form |
|---|---|---|---|---|
| Polyethylene Glycol 3350 | Carbowax ® | Union Carbide Corporation, Danbury, CT | 100 | 2042 |

A beaker was submersed in a 70° C. water bath (Ret digivisc; Antal-Direct, Wayne, Pa.). The polyethylene glycol (PEG) was added to the beaker and was mixed with a spatula until melted. The molten PEG was then introduced into a rubber capsule-shape mold (20.5 mm×12.6 mm×10.7 mm). A coated core containing a hole, prepared as described above, was inserted into the mold. Additional molten PEG was added to fill the mold. The mold was then allowed to cool for five minutes, hardening the PEG into a shell. The resulting dosage form comprising a PEG shell was removed from the mold.

The release profiles versus time for two dosage forms of the invention were compared with the release profile of an uncoated solid core material. The release profile (i.e. % released vs. time) for each is shown in FIG. 6. In FIG. 6, curve "c" is the release profile of the uncoated solid core, curve "b" is the release profile of the dosage form having a 0.397 cm hole, and curve "a" is the release profile of the dosage form having a 0.280 cm hole.

EXAMPLE 2

Dosage forms of the invention are made in a continuous process using an apparatus comprising three thermal cycle molding modules linked in series via two transfer devices as described at pages 14-16 of copending U.S. application Ser. No. 09/966,939, the disclosure of which is incorporated herein by reference. The dosage forms have the structure shown in FIG. 7 and each comprise a core having a toroidal shape (i.e., donut-shaped) coated first with an first coating on its entire exterior surface except for the surface inside the hole of the donut. The dosage forms further comprise a shell completely overlying the core and the first coating, thereby forming the outermost layer of the dosage form.

The core is made of a core flowable material comprising the following ingredients:

| Tablet | Trade Name | Manufacturer | Weight % | Mg/Tablet |
|---|---|---|---|---|
| Polyethylene Glycol 3350 | Carbowax ® | Union Carbide Corporation, Danbury, CT | 42.0 | 238 |
| Shellac Powder | Regular bleached shellac | Mantrose-Haeuser Company, Atteboro, MA | 10.0 | 56 |
| Croscarmellose Sodium | Ac-Di-Sol ® | FMC Corporation, Newark, DE | 21.0 | 119 |
| Pseudoephedrine Hydrochloride Crystal | | BASF PharmaChemikalien GmbH & Co., Ludwigshafen/Rhein. | 27.0 | 153 |

The ingredients are processed as set forth in Example 1.

The first coating is made from an first coating flowable material comprising the following ingredients:

| Granulation | Trade Name | Manufacturer | Weight % | Mg/dosage Formt |
|---|---|---|---|---|
| Polycaprolactones Isopropanol (dried as solvent) | CAPA 686 | Solvay Interox, Inc., Laporte, TX | 100 | 286 |

The polycaprolactones are first mixed with the isopropanol until a uniform dispersion is obtained.

The shell is made from a shell flowable material comprising the following ingredient:

| Shell | Trade Name | Manufacturer | Weight % | Mg/Dosage Form |
|---|---|---|---|---|
| Polyethylene Glycol 3350 | Carbowax ® | Union Carbide Corporation, Danbury, CT | 100 | 2042 |

The thermal cycle molding modules have the general configuration shown in FIG. 3 of copending U.S. application Ser. No. 09/966,939, which depicts a thermal cycle molding module 200 comprising a rotor 202 around which a plurality of mold units 204 are disposed. Each thermal cycle molding module includes its own reservoir 206 (see FIG. 4 of copending U.S. application Ser. No. 09/966,939) for holding the core flowable material, the first coating flowable material, and the shell flowable material, respectively. In addition, each thermal cycle molding module is provided with a temperature control system for rapidly heating and cooling the mold units. FIGS. 55 and 56 of copending U.S. application Ser. No. 09/966,939 depict the temperature control system 600.

The cores are made in a first thermal cycle molding module, which is linked via a first transfer device to a second thermal cycle molding module, which is in turn linked via a second transfer device to a third thermal cycle molding module. The first thermal cycle molding module has the specific configuration shown in FIG. 26A of copending U.S. application Ser. No. 09/966,939. The first thermal cycle molding module comprises center mold assemblies 212 and upper mold assemblies 214 as shown in FIG. 26C, which mate to form mold cavities having the shape of a donut. As rotor 202 rotates, the opposing center and upper mold assemblies close. Core flowable material, which is heated to a flowable state in reservoir 206, is injected into the resulting mold cavities. The temperature of the core flowable material is then decreased, hardening the core flowable material into donut-shaped cores. The mold assemblies open and eject the cores, which are received by the first transfer device.

Both the first and second transfer devices have the structure shown as 300 in FIG. 3 of copending U.S. application Ser. No. 09/966,939. Each comprises a plurality of transfer units 304 attached in cantilever fashion to a belt 312 as shown in FIGS. 68 and 69 of copending U.S. application Ser. No. 09/966,939. The transfer devices rotate and operate in sync with the thermal cycle molding modules to which they are coupled. Transfer units 304 comprise retainers 330 for holding the partially made dosage forms as they travel around each transfer device.

The first transfer device transfers the donut-shaped cores to the second thermal cycle molding module, which applies the first coating to the cores. The second thermal cycle molding module is of the type shown in FIG. 28A of copending U.S. application Ser. No. 09/966,939. The mold units 204 of the second thermal cycle molding module comprise upper mold assemblies 214, rotatable center mold assemblies 212 and lower mold assemblies 210 as shown in FIG. 28C. Donut-shaped cores are continuously transferred to the mold assemblies, which then close over the cores. First coating flowable material, which is heated to a flowable state in reservoir 206, is injected into the mold cavities created by the closed mold assemblies. The temperature of the first coating flowable material is then decreased, hardening it. The mold assemblies open and eject the partially coated cores, which are received by the second transfer device. Coating is performed in two steps, each half of the cores being coated separately as shown in the flow diagram of FIG. 28B of copending U.S. application Ser. No. 09/966,939 via rotation of the center mold assembly.

The construction of the mold assemblies in the second thermal cycle molding module is such that the portion of the donut-shaped cores inside the hole is masked by the mold assemblies during application of the first coating.

The inside surface of the mold assembly has a masking protrusion to cover the hole of the donut-shaped cores. Accordingly, the surface of the cores inside the hole remains uncoated upon exiting the second thermal cycle molding module.

The second transfer device carries the partially coated cores to the third thermal cycle molding module, which applies the shell. The third thermal cycle molding module is also of the type shown in FIGS. 28A-C of copending U.S. application Ser. No. 09/966,939 comprising rotatable center mold assemblies 212, lower mold assemblies 210 and upper mold assemblies 214. Cores bearing the first coating are continuously transferred to the mold assemblies of the third thermal cycle molding module. Shell flowable material, which is heated to a flowable state in reservoir 206, is injected into the mold cavities created by the closed mold assemblies holding the cores. The temperature of the shell flowable material is then decreased, hardening it. The mold assemblies open and eject the finished dosage forms. Shell coating is performed in two steps, each half of the dosage forms being coated separately as shown in the flow diagram of FIG. 28B of copending U.S. application Ser. No. 09/966,939 via rotation of the center mold assembly.

Although this invention has been illustrated by reference to specific embodiments, it will be apparent to those skilled in the art that various changes and modifications may be made which clearly fall within the scope of this invention.

The invention claimed is:

1. A dosage form comprising:
   (a) at least one active ingredient:
   (b) a core having a first surface portion upon which resides a first coating and a second surface portion which is substantially free of the first coating; and
   (c) a shell which resides upon at least part of both the first coating and the second surface portion of the core,
   wherein the shell comprises a different material from the first coating,
   wherein the core comprises a cavity, wherein the cavity is an aperture which extends entirely through the core,
   wherein at least a portion of the second surface portion of the core is located within the cavity, and
   wherein the shell resides upon at least a part of the second surface portion of the core which is located within the cavity.

2. The dosage form of claim 1, in which the shell resides over all the first coating and the second surface of the core.

3. The dosage form of claim 1, in which the shell comprises a material selected from water soluble or water swellable thermoplastic film formers, water soluble or water swellable thickeners, crystallizable and non-crystallizable carbohydrates.

4. The dosage form of claim 1, in which the shell comprises a thermal-reversible carrier selected from the group consisting of thermoplastic polyalkylene glycols, thermoplastic polyalkylene oxides, and combinations thereof.

5. A dosage form comprising: (a) at least one active ingredient; (b) a core comprising a center portion having an exterior surface and an annular portion having an exterior surface and an interior surface, wherein the annular portion interior surface is in contact with at least a portion of the center portion exterior surface, and a first coating resides on at least a portion of the annular portion exterior surface, and in which the core annular portion has the shape of a torus; and (c) a shell which resides upon at least a portion of the exterior surface of the center portion, wherein the shell comprises a different material than the first coating.

6. The dosage form of claim 1, in which the core comprises at least one active ingredient.

7. The dosage form of claim 5, in which the center portion of the core comprises at least one active ingredient.

8. The dosage form of claim 5, in which the annular portion of the core comprises at least one active ingredient.

9. The dosage form of claim 5, in which the center portion of the core comprises a first active ingredient and the annular portion of the core comprises a second active ingredient.

10. The dosage form of claim 1, in which the shell comprises at least one active ingredient.

11. The dosage form of claim 1, in which both the shell and the core each comprise at least one active ingredient.

12. The dosage form of claim 5, in which the first coating resides upon the entire annular portion exterior surface.

13. The dosage form of claim 12, in which the shell resides upon the entire first coating and the center portion surface.

14. The dosage form of claim 5, which the shell comprises a material selected from water soluble or water swellable thermoplastic film formers, water soluble or water swellable thickeners, crystallizable and non-crystallizable carbohydrates.

15. The dosage form of claim 5, in which the shell comprises a thermal-reversible carrier selected from the group consisting of thermoplastic polyalkylene glycols, thermoplastic polyalkylene oxides, and combinations thereof.

16. A dosage form comprising: (a) at least one active ingredient; (b) a core having an outer surface and a cavity which extends through the core having the shape of a torus such that the core outer surface has at least a first opening therein; (c) a first coating which resides on at least a portion of the core outer surface, wherein the first shell portion comprises a different material from the first coating; and (d) a first shell portion which is adjacent to the first opening and covers at least the first opening.

17. The dosage form of claim 16, in which the cavity extends entirely through the core such that the core has first and second openings therein, the first shell portion is adjacent to and covers at least the first opening, and the dosage form additionally comprises a second shell portion which is adjacent to and covers at least the second opening, wherein the first and second shell portions each comprise a material different from the first coating.

18. The dosage form of claim 16, in which the first shell portion comprises at least one water soluble material.

19. The dosage form of claim 16, in which the second shell portion comprises at least one water soluble material.

20. The dosage form of claim 16, in which the first and second shell portions each comprise at least one water soluble material.

21. The dosage form of claim 16, in which the first shell portion or the core or a combination thereof comprises at least one active ingredient.

22. The dosage form of claim 16, in which the first shell portion, second shell portion or the core or a combination thereof comprises at least one active ingredient.

23. The dosage form of claim 16, in which the first shell portion resides upon at least a portion of the first coating.

24. The dosage form of claim 22, in which the shell resides upon the entire outer surface of the first coating.

25. The dosage form of claim 1, in which at least a portion of the active ingredient is released in a sustained manner.

26. The dosage form of claim 24, in which the dosage form releases at least a portion of the active ingredient at a substantially constant rate.

27. The dosage form of claim 5, in which the center portion of the core provides a time delay to the release of active ingredient from the annular portion of the core.

28. The dosage form of claim 1, in which the core functions as an eroding matrix.

29. The dosage form of claim 1, in which the core functions as a diffusional matrix for the release of active ingredient contained therein.

30. The dosage form of claim 1, in which the core comprises a release-modifying excipient selected from the group consisting of swellable erodible hydrophilic materials, insoluble edible materials, pH-dependent polymers, and mixtures thereof.

31. The dosage form of claim 1, in which the first coating comprises at least about 30 weight percent of a thermal reversible carrier, based on the weight of the first coating.

32. The dosage form of claim 1, in which the first coating comprises at lease about 10 weight percent of a film former selected from the group consisting of film-forming water soluble polymers, film-forming proteins, film-forming water insoluble polymers, and film-forming pH-dependent polymers, and combinations thereof.

33. The dosage form of claim 1, in which the shell or shell portion comprises thermoplastic polyalkylene glycols, thermoplastic polyalkylene oxides, and combinations thereof.

34. The dosage form of claim 1, in which the shell portion is breached or dissolved within 30 minutes in 900 ml water or 0.1 N HCl, or phosphate buffer solution at 37° C. with stirring by a USP type 2 (Paddle method) at 50 or 100 rpm.

35. The dosage form of claim 1, in which the release of at least one active ingredient follows a double pulse profile.

36. The dosage form of claim 1, in which the release of at least one active ingredient follows a delayed then sustained release profile.

37. The dosage form of claim 1, in which the release of one or more active ingredients follows a zero-order, first-order, or square root of time profile.

38. The dosage form of claim 1, in which the shell is substantially free of pores in the diameter range of 0.5 to 5.0 microns.

39. The dosage form of claim 1, in which the first coating comprises up to about 55 weight percent of a release-modifying excipient selected from water-insoluble polymers and low-melting hydrophobic materials and combinations thereof.

40. The dosage form of claim 39, in which the release-modifying excipient is a polycaprolactone.

* * * * *